(12) United States Patent
Luly et al.

(10) Patent No.: US 6,503,926 B2
(45) Date of Patent: *Jan. 7, 2003

(54) CHEMOKINE RECEPTOR ANTAGONISTS AND METHODS OF USE THEREFOR

(75) Inventors: Jay R. Luly, Wellesley, MA (US); Yoshisuke Nakasato, Shizuoka (JP); Etsuo Ohshima, Nagareyama (JP); Hiroki Sone, Shizuoka (JP); Osamu Kotera, Shizuoka (JP); Geraldine C. B. Harriman, Charlestown, RI (US)

(73) Assignees: Millennium Pharmaceuticals, Inc., Cambridge, MA (US); Kyowa Hakko Kogyo Co., Ltd., Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/362,796

(22) Filed: Jul. 28, 1999

(65) Prior Publication Data

US 2002/0161005 A1 Oct. 31, 2002

Related U.S. Application Data

(63) Continuation-in-part of application No. 09/235,111, filed on Jan. 21, 1999, now Pat. No. 6,288,084, which is a continuation-in-part of application No. 09/148,236, filed on Sep. 4, 1998, now Pat. No. 6,288,083.

(51) Int. Cl.[7] .................. A61K 31/4545; A61K 31/438; C07D 401/14; C07D 405/14; C07D 409/14; A61P 29/00; A61P 37/08

(52) U.S. Cl. ............ 514/318; 514/252.03; 514/235.01; 514/255.05; 514/257; 514/259; 514/278; 514/326; 546/194; 546/16; 546/17; 546/18; 546/209; 546/210; 546/211; 546/212; 546/213; 546/214; 546/193; 544/129; 544/238; 544/360; 544/333; 544/405; 544/231; 544/71

(58) Field of Search .............................. 546/194, 16–18, 546/209, 210, 211, 212, 213, 214, 193; 514/318, 252.03, 235.5, 253.01, 255.05, 257, 259, 278, 326; 544/129, 238, 360, 333, 405, 231, 71

(56) References Cited

U.S. PATENT DOCUMENTS

| | | | |
|---|---|---|---|
| 2,712,020 A | 6/1955 | Adamson | 260/294.8 |
| 3,238,216 A | 3/1966 | Janssen | 260/293.4 |
| 3,770,729 A | 11/1973 | Nakanishi et al. | 260/240 |
| 3,940,386 A | 2/1976 | Szabo et al. | |
| 4,206,213 A * | 6/1980 | Kleeman | 424/250 |
| 4,250,176 A | 2/1981 | Vandenberk et al. | 424/250 |
| 4,547,496 A | 10/1985 | Kumazawa et al. | 514/218 |
| 4,931,450 A | 6/1990 | Sonnewald | 514/326 |
| 5,010,090 A * | 4/1991 | Gronvald | 514/326 |
| 5,801,175 A | 9/1998 | Afonso et al. | 514/254 |

FOREIGN PATENT DOCUMENTS

| | | |
|---|---|---|
| CZ | 240 698 | 6/1987 |
| DE | 80449 | 9/1969 |
| DE | 2 162 802 | 9/1972 |
| DE | 24 31 178 A1 | 1/1975 |
| DE | 28 00 535 A1 | 7/1978 |
| EP | 0029420 | 5/1981 |
| EP | 0 270 692 A1 | 6/1988 |
| FR | 1 462 206 A | 12/1966 |
| GB | 1320481 | 6/1973 |
| JP | 5661373 | 5/1981 |
| JP | 05043548 | 2/1993 |
| WO | WO 96/31469 | 10/1996 |
| WO | WO 96/31470 | 10/1996 |
| WO | WO 96/31498 | 10/1996 |
| WO | WO 97/24325 | 7/1997 |
| WO | WO 97/44329 | 11/1997 |
| WO | WO 98/04554 | 2/1998 |
| WO | WO 98/11092 | 3/1998 |
| WO | WO 98/11093 | 3/1998 |
| WO | WO 98/11096 | 3/1998 |
| WO | WO 98/11097 | 3/1998 |
| WO | WO 98/11098 | 3/1998 |
| WO | WO 98/11099 | 3/1998 |
| WO | WO 98/11106 | 3/1998 |
| WO | WO 98/25604 | 6/1998 |
| WO | WO 98/25605 | 6/1998 |
| WO | WO 98/25617 | 6/1998 |
| WO | WO 98/27815 | 7/1998 |
| WO | WO 00/14086 | 3/2000 |

OTHER PUBLICATIONS

Sato M et al. Chem. Pharm. Bull. (1978), 26(11), 3296–3305.*

Adamson DW. et al. J. Chem. Soc. (1958), pp. 312–324.*

(List continued on next page.)

*Primary Examiner*—Evelyn Mei Huang
(74) *Attorney, Agent, or Firm*—Hamilton, Brook, Smith & Reynolds, P.C.

(57) ABSTRACT

Disclosed are novel compounds and a method of treating a disease associated with aberrant leukocyte recruitment and/or activation. The method comprises administering to a subject in need an effective amount of a compound represented by:

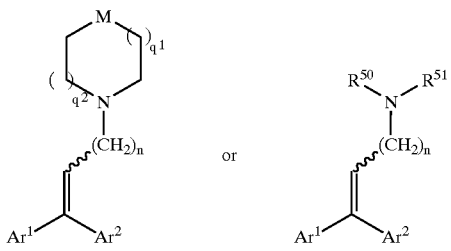

and physiologically acceptable salts thereof.

37 Claims, 31 Drawing Sheets

OTHER PUBLICATIONS

Sindelar, Karel, et al., "Potential Antidiarrheal Agents:1–(11–Cyano–6,11–Dihydrodibenzo [b,e] Thiepin–11YL–Alklyl)– and 1–(10–Cyano–10,11–Dihydrodibenzo[b,f]Thiepin–10–YL–Alkyl)–4–Substituted Piperidines," *Collection Czechoslovak Chem. Commun.*, 50:1089–1096 (1985).

Chemical Abstracts, 121(3) :35275n (1994).

Sindelar, Karel, et al., "Antihistamine Substances: Tricyclic Analogues of N–(4,4–Diphenyl–3Butene–1YL)Nipecotic Acid and Some Related Compounds," *Collection Czechoslovak Chem. Commun.*,59:667–674 (1994).

Davis, M. A. et al., "New Psychotropic Agents.VIII Analogs of Amitriptyline Containing Normeperidine Group," *New Psychotropic Agents VIII.*, pp. 627–635 (Jul. 1967).

Helwig, H., et al.," Helwig/Otto Arzneimittal", *Arzneimittal*, 1:4–1 through 4–24, 8th Ed., (1992).

Ali, Fadia E., et al., "Orally Active and Potent Inhibitors of γ–Aminobutyric Acid Uptake," *J. Med. Chem.* 28:653–660 (1985).

Sindelar, Karel, et al., "Potential Antihistaminics: Tricyclic Carboxylic Acids Derived From 6,11–Dihydrodibenzo[b,e] Thiepine and 4,9–Dihydrothieno[2,3–c]–2–Benzothiepine," *Collection Czechoslovak Chem. Commun.* 56–2482–2493 (1991).

Polivka, Zdenek, et al., "Heterocyclic Ethers Derived From 6,11–Dihydrodibenzo–[b,e]Thiepin–11–OLS and 4,9–Dihydrothieno[2,3–c]–2–Benzothiepin–4–OL; a New Series of Potential Antidepressants and Antihistamine Agents," *Collection Czechoslovak Chem. Commun.* 51:2034–2049 (1986).

Polivka, Zdenek, et al., "Antiaminic Agents Derived from Thieno[2,3–c]–2–Benzothiepin: 4–(1–Methyl–4–Piperidylidene)–4,9–Dihydrothieno[2,3–c] –2–Benzothiepin and Some Related Compounds," *Collection Czechoslovak Chem. Commun.* 48:623–641 (1983).

Rajsner, M., et al., "Neurotropic and Psychotropic Comounds.XXXI Chemistry and Pharamacology of 11–(3–Dimethylaminopropylidene)–2–Mehtyl–6,11–Dihydrodibenzo[b,e] Thiepin and of Some Analogues," *Collection Czechoslovak Chem. Commun.* 34:1015–1024 (1969).

Rajsner, M., et al.,"Neurotrope und Psychotrope Substanzen XV. 4,9–Dihydrothieno[2,3–b]Benzo[e]Thiepin–Derivate," *Collection Czechoslovak Chem. Commun.* 32:2854–2866 (1967).

Hesselgesser, Joseph, et al., "Identification and Characterization of Small Molecule Functional Antagonists of the CCR1 Chemokine Receptor", *The Journal of Biological Chemistry*, 273(25):15687–15692 (Jun. 19, 1998).

XP–002103024, Database WPI, Section Ch, Week 8128, Derwent Publications Ltd., London, GB; AN 81–50785D and JP 56 061373 A (Hokuriku Pharm Co., Ltd.) May 26, 1981.

Ng, H.P. et al., "Discovery of Novel Non–Peptide CCR1 Receptor Antagonists," *J. Med. Chem.*, 42:4680–4694 (1999).

Bengtsson, B.O. et al., Chemical Abstracts, 117:143039 (1992).

Hoegberg, T. and Ulff, B., Chemical Abstracts, 101:190727 (1984).

* cited by examiner

Example 81

Example 82

Example 83

Example 84

Example 85

Example 86

Example 87

Example 88

Example 89

Example 90

Example 91

Example 92

Example 93

Example 94

Example 95

Example 96

Example 97

Example 98

Example 99

Example 100

Example 111

Example 112

Example 113

Example 114

Example 115

Example 116

Example 117

Example 118

Example 119

Example 120

Example 139  Example 251400  Example 141

Example 142  Example 143  Example 144

Example 145  Example 146  Example 147

Example 148  Example 149

Example 150

Example 151

Example 152

| | $R^{40}$ |
|---|---|
| Example 206 |  |
| Example 207 |  |
| Example 208 |  |
| Example 209 |  |
| Example 210 |  |
| Example 211 |  |
| Example 212 |  |

|  | R$^1$ | R$^{40}$ |
|---|---|---|
| Example 213 | -CN | -OCH$_3$ |
| Example 214 | -CH$_2$NH$_2$ | -OCH$_3$ |
| Example 215 | -NH$_2$ | -OCH$_3$ |
| Example 216 | -CH$_3$ | -OCH$_3$ |
| Example 217 | -OCH$_3$ | -OCH$_3$ |
| Example 218 | -F | -OH |
| Example 219 | -CH$_3$ | -OH |
| Example 210 | -CH$_3$ |  |

| | $R^{50}$ | $R^{51}$ |
|---|---|---|
| Example 221 |  | -H |
| Example 222 |  | -H |
| Example 223 |  | -CH$_3$ |
| Example 224 |  | -CH$_3$ |
| Example 225 |  | -CH$_3$ |
| Example 226 |  | -CH$_3$ |
| Example 227 |  | |

|  | R¹ | R² |
|---|---|---|
| Example 228 | -OH |  |
| Example 229 | -H |  |
| Example 230 | -H |  |
| Example 231 | -OH |  |
| Example 232 |  | |

$R^{40}$

Example 233

Example 234

CHEMOKINE RECEPTOR ANTAGONISTS AND METHODS OF USE THEREFOR

RELATED APPLICATION

This application is a continuation-in-part of U.S. Ser. No. 09/235,111, filed Jan. 21, 1999, now U.S. Pat. No. 6,288,084 which is a continuation-in-part of U.S. Ser. No. 09/148,236, filed Sep. 4, 1998 now U.S. Pat. No. 6,288,083; the entire teachings of the above-referenced applications are incorporated herein by reference.

BACKGROUND OF THE INVENTION

Chemoattractant cytokines or chemokines are a family of proinflammatory mediators that promote recruitment and activation of multiple lineages of leukocytes and lymphocytes. They can be released by many kinds of tissue cells after activation. Continuous release of chemokines at sites of inflammation mediates the ongoing migration of effector cells in chronic inflammation. The chemokines characterized to date are related in primary structure. They share four conserved cysteines, which form disulfide bonds. Based upon this conserved cysteine motif, the family is divided into two main branches, designated as the C-X-C chemokines (α-chemokines), and the C-C chemokines (β-chemokines), in which the first two conserved cysteines are separated by an intervening residue, or adjacent respectively (Baggiolini, M. and Dahinden, C. A., *Immunology Today*, 15:127–133 (1994)).

The C-X-C chemokines include a number of potent chemoattractants and activators of neutrophils, such as interleukin 8 (IL-8), PF4 and neutrophil-activating peptide-2 (NAP-2). The C-C chemokines include RANTES (Regulated on Activation, Normal T Expressed and Secreted), the macrophage inflammatory proteins 1α and 1β (MIP-1α and MIP-1β), eotaxin and human monocyte chemotactic proteins 1–3 (MCP-1, MCP-2, MCP-3), which have been characterized as chemoattractants and activators of monocytes or lymphocytes but do not appear to be chemoattractants for neutrophils. Chemokines, such as RANTES and MIP-1α, have been implicated in a wide range of human acute and chronic inflammatory diseases including respiratory diseases, such as asthma and allergic disorders.

The chemokine receptors are members of a superfamily of G protein-coupled receptors (GPCR) which share structural features that reflect a common mechanism of action of signal transduction (Gerard, C. and Gerard, N. P., *Annu Rev. Immunol.*, 12:775–808 (1994); Gerard, C. and Gerard, N. P., *Curr. Opin. Immunol.*, 6:140–145 (1994)). Conserved features include seven hydrophobic domains spanning the plasma membrane, which are connected by hydrophilic extracellular and intracellular loops. The majority of the primary sequence homology occurs in the hydrophobic transmembrane regions with the hydrophilic regions being more diverse. The first receptor for the C-C chemokines that was cloned and expressed binds the chemokines MIP-1α and RANTES. Accordingly, this MIP-1α/RANTES receptor was designated C-C chemokine receptor 1 (also referred to as CCR-1; Neote, K., et al., *Cell*, 72:415–425 (1993); Horuk, R. et al., WO 94/11504, May 26, 1994; Gao, J.-I. et al., *J. Exp. Med.*, 177:1421–1427 (1993)). Three receptors have been characterized which bind and/or signal in response to RANTES: CCR3 mediates binding and signaling of chemokines including eotaxin, RANTES, and MCP-3 (Ponath et al., *J. Exp. Med.*, 183:2437 (1996)), CCR4 binds chemokines including RANTES, MIP-1α, and MCP-1 (Power, et al., *J. Biol. Chem.*, 270:19495 (1995)), and CCR5 binds chemokines including MIP-1α, RANTES, and MIP-1β (Samson, et al., *Biochem.* 35: 3362–3367 (1996)). RANTES is a chemotactic chemokine for a variety of cell types, including monocytes, eosinophils, and a subset of T-cells. The responses of these different cells may not all be mediated by the same receptor, and it is possible that the receptors CCR1, CCR4 and CCR5 will show some selectivity in receptor distribution and function between leukocyte types, as has already been shown for CCR3 (Ponath et al.). In particular, the ability of RANTES to induce the directed migration of monocytes and a memory population of circulating T-cells (Schall, T. et al., *Nature*, 347:669–71 (1990)) suggests this chemokine and its receptor(s) may play a critical role in chronic inflammatory diseases, since these diseases are characterized by destructive infiltrates of T cells and monocytes.

Many existing drugs have been developed as antagonists of the receptors for biogenic amines, for example, as antagonists of the dopamine and histamine receptors. No successful antagonists have yet been developed to the receptors for the larger proteins such as chemokines and C5a. Small molecule antagonists of the interaction between C-C chemokine receptors and their ligands, including RANTES and MIP-1α, would provide compounds useful for inhibiting harmful inflammatory processes "triggered" by receptor ligand interaction, as well as valuable tools for the investigation of receptor-ligand interactions.

SUMMARY OF THE INVENTION

It has now been found that a class of small organic molecules are antagonists of chemokine receptor function and can inhibit leukocyte activation and/or recruitment. An antagonist of chemokine receptor function is a molecule which can inhibit the binding and/or activation of one or more chemokines, including C-C chemokines such as RANTES, MIP-1α, MCP-2, MCP-3 and MCP-4 to one or more chemokine receptors on leukocytes and/or other cell types. As a consequence, processes and cellular responses mediated by chemokine receptors can be inhibited with these small organic molecules. Based on this discovery, a method of treating a disease associated with aberrant leukocyte recruitment and/or activation is disclosed as well as a method of treating a disease mediated by chemokine receptor function. The method comprises administering to a subject in need an effective amount of a compound or small organic molecule which is an antagonist of chemokine receptor function. Compounds or small organic molecules which have been identified as antagonists of chemokine receptor function are discussed in detail herein below, and can be used for the manufacture of a medicament for treating or for preventing a disease associated with aberrant leukocyte recruitment and/or activation. The invention also relates to the disclosed compounds and small organic molecules for use in treating or preventing a disease associated with aberrant leukocyte recruitment and/or activation. The invention also includes pharmaceutical compositions comprising one or more of the compounds or small organic molecules which have been identified herein as antagonists of chemokine function and a suitable pharmaceutical carrier. The invention further relates to novel compounds which can be used to treat an individual with a disease associated with aberrant leukocyte recruitment and/or activation and methods for their preparation.

BRIEF DESCRIPTION OF THE DRAWINGS

In FIG. 10C, $R^{40}$ is represented by $-(O)_u-(CH_2)_t-C(O)-NR^{21}R^{22}$, u is one, t is zero.

DETAILED DESCRIPTION OF THE INVENTION

Figure 1:
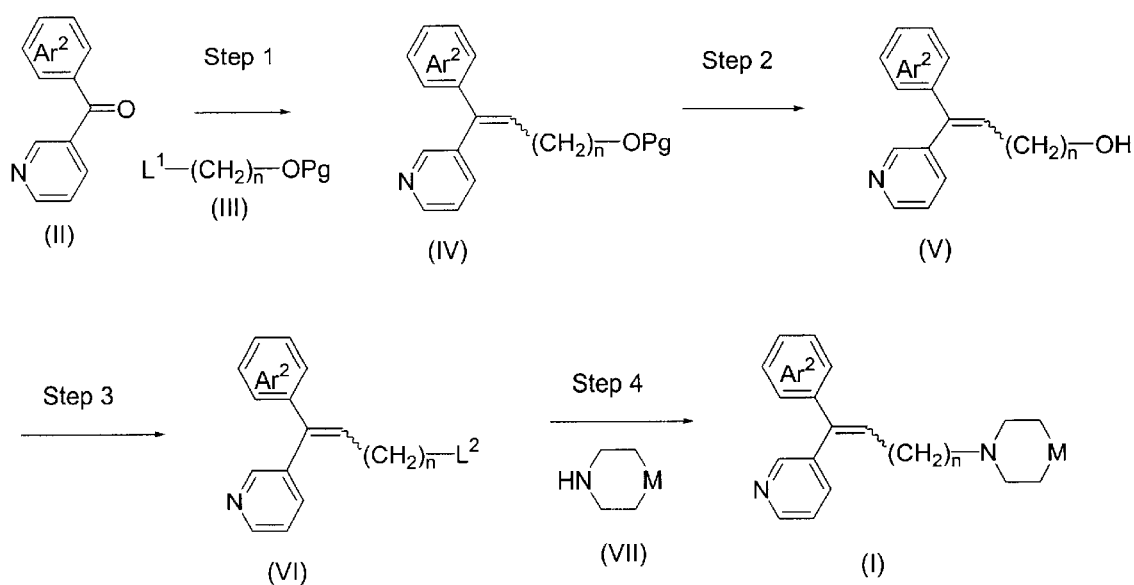
FIG. 1 is a schematic showing the preparation of the compounds represented by Structural Formula (I).

The present invention relates to small molecule compounds which are modulators of chemokine receptor function. In a preferred embodiment, the small molecule compounds are antagonists of chemokine receptor function. Accordingly, processes or cellular responses mediated by the binding of a chemokine to a receptor can be inhibited (reduced or prevented, in whole or in part), including leukocyte migration, integrin activation, transient increases in the concentration of intracellular free calcium $[Ca^{++}]_i$, and/or granule release of proinflammatory mediators.

The invention further relates to a method of treatment, including prophylactic and therapeutic treatments, of a disease associated with aberrant leukocyte recruitment and/or activation or mediated by chemokines or chemokine receptor function, including chronic inflammatory disorders characterized by the presence of RANTES, MIP-1α, MCP-2, MCP-3 and/or MCP-4 responsive T cells, monocytes and/or eosinophils, including but not limited to diseases such as arthritis (e.g., rheumatoid arthritis), atherosclerosis, arteriosclerosis, restenosis, ischemia/reperfusion injury, diabetes mellitus (e.g., type 1 diabetes mellitus), psoriasis, multiple sclerosis, inflammatory bowel diseases such as ulcerative colitis and Crohn's disease, rejection of transplanted organs and tissues (i.e., acute allograft rejection, chronic allograft rejection), graft versus host disease, as well as allergies and asthma. Other diseases associated with aberrant leukocyte recruitment and/or activation which can be treated (including prophylactic treatments) with the methods disclosed herein are inflammatory diseases associated with Human Immunodeficiency Virus (HIV) infection, e.g., AIDS associated encephalitis, AIDS related maculopapular skin eruption, AIDS related interstitial pneumonia, AIDS related enteropathy, AIDS related periportal hepatic inflammation and AIDS related glomerulo nephritis. The method comprises administering to the subject in need of treatment an effective amount of a compound (i.e., one or more compounds) which inhibits chemokine receptor function, inhibits the binding of a chemokine to leukocytes and/or other cell types, and/or which inhibits leukocyte migration to, and/or activation at, sites of inflammation.

The invention further relates to methods of antagonizing a chemokine receptor, such as CCR1, in a mammal comprising administering to the mammal a compound as described herein.

According to the method, chemokine-mediated chemotaxis and/or activation of pro-inflammatory cells bearing receptors for chemokines can be inhibited. As used herein, "pro-inflammatory cells" includes but is not limited to leukocytes, since chemokine receptors can be expressed on other cell types, such as neurons and epithelial cells.

While not wishing to be bound by any particular theory or mechanism, it is believed that compounds of the invention are antagonists of the chemokine receptor CCR1, and that therapeutic benefits derived from the method of the invention are the result of antagonism of CCR1 function. Thus, the method and compounds of the invention can be used to treat a medical condition involving cells which express CCR1 on their surface and which respond to signals transduced through CCR1, as well as the specific conditions recited above.

In one embodiment, the antagonist of chemokine receptor function is represented by Structural Formula (I):

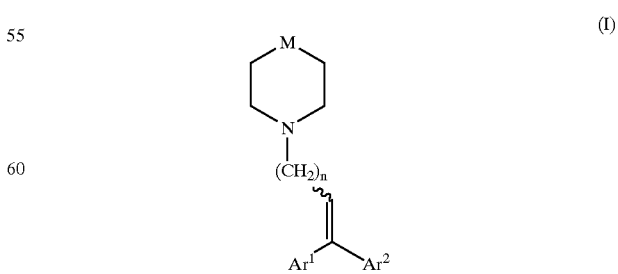

and physiologically acceptable salts thereof.

$Ar^1$ is a heteroaryl group, and

Ar² is a carbocyclic aromatic or heteroaryl group.

n is an integer, such as an integer from one to about four. Preferably, n is one, two or three. More preferably n is two. In alternative embodiments, other aliphatic or aromatic spacer groups (L) can be employed for $(CH_2)_n$.

M is >NR² or >CR¹R². M is preferably >C(OH)R².

R¹ is —H, —OH, —N₃, halogen, an aliphatic group, a substituted aliphatic group, an aminoalkyl group, —O— (aliphatic group), —O-(substituted aliphatic group), —SH, —S-(aliphatic group), —S-(substituted aliphatic group), —OC(O)-(aliphatic group), —O—C(Q)-(substituted aliphatic group), —C(O)O-(aliphatic group), —C(O)O-(substituted aliphatic group), —COOH, —CN, —CO—NR³R⁴, —NR³R⁴; or R¹ can be a covalent bond between the ring atom at M and an adjacent carbon atom in the ring which contains M. R¹ is preferably —H or —OH.

R² is —H, —OH, an acyl group, a substituted acyl group, —NR⁵R⁶, an aliphatic group, a substituted aliphatic group, an aromatic group, a substituted aromatic group, a benzyl group, a substituted benzyl group, a non-aromatic heterocyclic group, a substituted non-aromatic heterocyclic group —O-(substituted or unsubstituted aromatic group) or —O-(substituted or unsubstituted aliphatic group). R² is preferably an aromatic group or a substituted aromatic group.

R³, R⁴, R⁵ and R⁶ are independently —H, an acyl group, a substituted acyl group, an aliphatic group, a substituted aliphatic group, an aromatic group, a substituted aromatic group, a benzyl group, a substituted benzyl group, a non-aromatic heterocyclic group or a substituted non-aromatic heterocyclic group.

R¹ and R², R³ and R⁴, or R⁵ and R⁶ taken together with the atom to which they are bonded, can alternatively form a substituted or unsubstituted non-aromatic carbocyclic or heterocyclic ring.

In embodiments where M is >CR¹R² and R¹ is a covalent bond between the carbon atom at M and an adjacent carbon atom in the ring which contains M, the antagonist of chemokine function can be represented by Structural Formula (Ia).

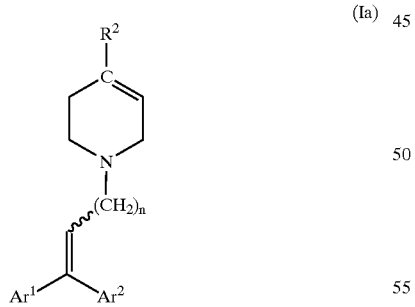
(Ia)

Ar¹, Ar², n and R² are as described in Structural Formula (I).

Ar¹ and Ar² in Structural Formula (I) can be independently substituted or unsubstituted. Suitable substituents are as described herein below. In one example, Ar¹ and/or Ar² is substituted with —(O)ᵤ—(CH₂)ₜ—C(O)OR²⁰, —(O)ᵤ—(CH₂)ₜ—OC(O) R²⁰, —(O)ᵤ—(CH₂)ₜ—C(O)—NR²¹R²² or —(O)ᵤ—(CH₂)ₜ—NHC(O)—O—R²⁰.

u is zero or one.

t is an integer, such as an integer from zero to about three. The methylene group, —(CH₂)ₜ—, can be substituted as described herein for aliphatic groups, or unsubstituted.

R²⁰, R²¹ or R²² are independently —H, an aliphatic group, a substituted aliphatic group, an aromatic group, a substituted aromatic group or a non-aromatic heterocyclic group. Alternatively, R²¹ and R²², taken together with the nitrogen atom to which they are bonded, form a non-aromatic heterocyclic ring.

In one embodiment, Ar¹ is a 3-pyridyl group, Ar² is a carbocyclic aromatic or heteroaromatic group and Ar¹ and Ar² are independently substituted or unsubstituted.

In a preferred embodiment the antagonist of chemokine receptor function is represented by Structural Formula (II), wherein Ar¹ is a 3-pyridyl group, Ar² is a phenyl group and Ar¹ and Ar² are independently substituted or unsubstituted.

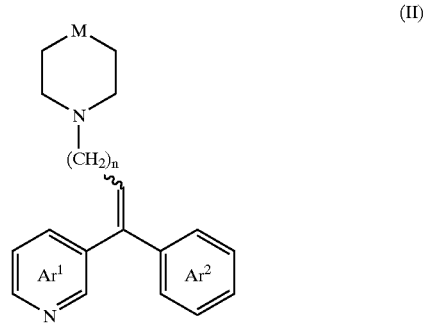
(II)

Preferably Ar² in Structural Formula (II) bears a meta substituent, R⁴⁰, and the antagonist of chemokine receptor unction is represented by Structural Formula (III):

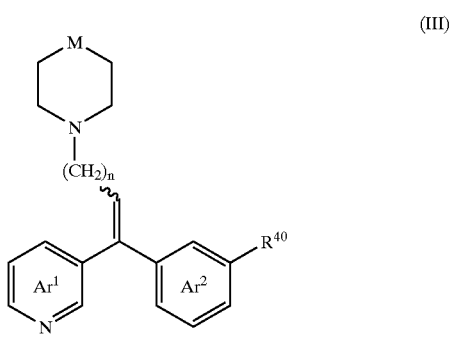
(III)

wherein R⁴⁰ is a substituent as described herein for aromatic groups, for example, —OH, halogen, —NO₂, —COOH, —NR²⁴R²⁵, —CONR²⁴R²⁵, a substituted or unsubstituted aliphatic group, a substituted or unsubstituted aromatic group, Q-(aliphatic group), Q-(substituted aliphatic group), —O-(aliphatic group), —O-(substituted aliphatic group), —O-(aromatic group), —O-(substituted aromatic group), an electron withdrawing group, —(O)ᵤ—(CH₂)ₜ—C(O)OR²⁰, —(O)ᵤ—(CH₂)ₜ—OC(O)R²⁰, —(O)ᵤ—(CH₂)ₜ—C(O)—NR²¹R²² or —(O)ᵤ—(CH₂)ₜ—NHC(O)—O—R²⁰.

u is zero or one.

t is an integer, such as an integer from zero to about three.

R²⁰, R²¹ or R²² are independently —H, an aliphatic group, a substituted aliphatic group, an aromatic group, a substituted aromatic group or a non-aromatic heterocyclic group. Alternatively, R²¹ and R²², taken together with the nitrogen atom to which they are bonded, form a non-aromatic heterocyclic ring.

$R^{24}$ and $R^{25}$ are independently —H, —OH, an aliphatic group, a substituted aliphatic group, a benzyl group, an aryl group or non-aromatic heterocyclic group or $R^{24}$ and $R^{25}$ taken together with the nitrogen atom to which they are bonded can form a substituted or unsubstituted non-aromatic heterocyclic ring.

Preferably $R^{40}$ is an aliphatic group, substituted aliphatic group, —O-(aliphatic group) or —O-(substituted aliphatic group). More preferably, $R^{40}$ is —O-alkyl, such as —O—$CH_3$, —O—$C_2H_5$, —O—$C_3H_7$ or —O—$C_4H_9$.

In another embodiment, $R^{40}$ can be represented by —(O)$_u$—(CH$_2$)$_t$—C(O)—NR$^{21}$R$^{22}$, wherein u is one, t is zero, and $R^{21}$ and $R^{22}$ are as described herein. In this embodiment, $R^{21}$ and $R^{22}$ can each independently be —H, a substituted or unsubstituted aliphatic group, a substituted or unsubstituted aromatic group, or $R^{21}$ and $R^{22}$ taken together with the nitrogen atom to which they are bonded form a nonaromatic heterocyclic ring (e.g., pyrrolidine, piperidine, morpholine).

In another embodiment, $R^{40}$ can be represented by —(O)$_u$—(CH$_2$)$_t$—C(O)—NR$^{21}$R$^{22}$, wherein u is zero, t is one to about three, and $R^{21}$ and $R^{22}$ are as described herein.

In another embodiment, $R^{40}$ can be represented by —(O)$_u$—(CH$_2$)$_t$—C(O)—NR$^{21}$R$^{22}$, wherein both u and t are zero, and $R^{21}$ and $R^{22}$ are as described herein.

In another embodiment, $R^{40}$ is an aliphatic group (e.g., methyl, ethyl, propyl) that is substituted with —NR$^{24}$R$^{25}$ or —CONR$^{24}$R$^{25}$, wherein $R^{24}$ and $R^{25}$ are as described herein. For example, $R^{40}$ can be represented by

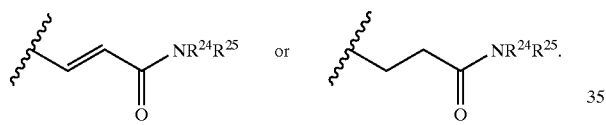

In a preferred embodiment, the chemokine receptor antagonist can be represented by Structural Formula (III) wherein n is three, M is C(OH)R$^2$ and $R^2$ is a phenyl group or a halophenyl group (e.g., 4-chlorophenyl). In one example of this embodiment, $R^{40}$ can be —O-(substituted aliphatic group), such as

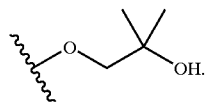

In another example, $R^{40}$ can be —COOH.

In another embodiment, the antagonist of chemokine activity is represented by Structural Formula (IV):

(IV)

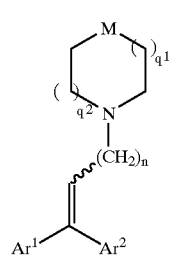

and physiologically acceptable salts thereof.

Ar$^1$, Ar$^2$ and n are as described in Structural Formula (I).

M is >NR$^2$, >CR$^1$R$^2$, —O—CR$^1$R$^2$—O— or —CH$_2$—CR$^1$R$^2$—O—.

$R^1$ and $R^2$ are as described in Structural Formula (I).

$q^1$ is an integer, such as an integer from zero to about three, and $q^2$ is an integer from zero to about one. The ring containing M can be substituted or unsubstituted.

Thus, the antagonist of chemokine function can be represent by, for example, Structural Formulas (IVa)–(IVk):

(IVa)

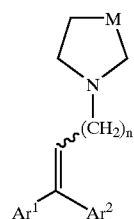

(IVb)

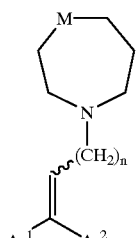

(IVc)

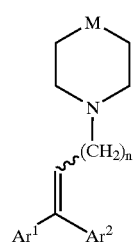

(IVd)

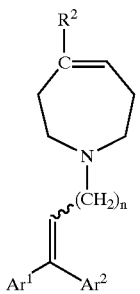

(IVe)

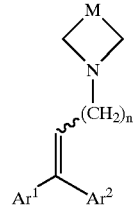

(IVf)
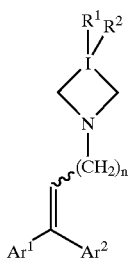

(IVg)
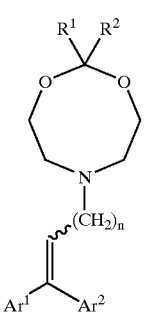

(IVh)
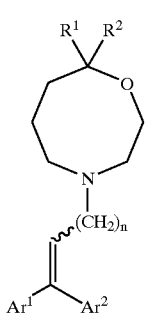

(IVi)
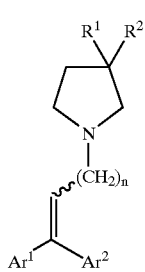

(IVj)
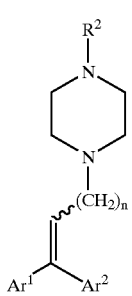

(IVk)
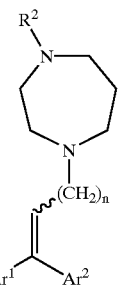

and physiologically acceptable salts thereof, wherein $Ar^1$, $Ar^2$, n and M are as described in Structural Formula (IV), and the ring which contains M is substituted or unsubstituted. The ring containing M can have one or more suitable substituents which are the same or different. Suitable substituents for the ring which contains M and other nonaromatic heterocyclic rings are as described herein. For example, the ring containing M can be substituted with a methyl, ethyl, propyl, butyl or oxo group.

The nitrogen atom in the ring containing M can be a tertiary nitrogen as depicted in Structural Formula (IV), or the nitrogen atom can be quaternized with a suitable substituent, such as a $C_1$ to about $C_6$ or a $C_1$ to about $C_3$ substituted or unsubstituted aliphatic group. Compounds which comprise a quaternary nitrogen atom can also contain a counteranion such as chloride, bromide, iodide, acetate, perchlorate and the like.

The antagonist of chemokine function can be represented by Structural Formula (IV) wherein the heterocyclic ring containing M is substituted with a suitable bivalent group which is bonded to two atoms that are in the ring, thereby forming a bicyclic moiety. Suitable bivalent groups include, for example, substituted or unsubstituted bivalent aliphatic groups, such as a $C_1$–$C_6$ alkylene group.

The antagonist of chemokine receptor function can comprise a variety of bicyclic moieties. In one embodiment, the antagonist of chemokine receptor function can be represented by Structural Formula (V):

(V)
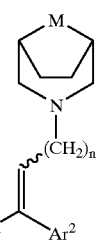

and physiologically acceptable salts thereof.

M is $>NR_2$, $>CR^1R^2$, $—O—CR^1R^2—O—$ or $—CH_2—CR^1R^2—O—$. Preferably, M is $>NR^2$ or $>CR^1R^2$. $Ar^1$, $Ar^2$, $R^1$, $R^2$ and n are as described in Structural Formula (I).

In another embodiment, the antagonist of chemokine receptor function is represented by Structural Formula (VI):

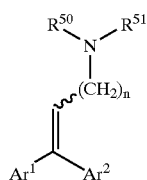

(VI)

and physiologically acceptable salts thereof.

Ar¹ and Ar² are as described in Structural Formula (I).

n is an integer, such as an integer from one to about four. Preferably, n is one, two or three. More preferably n is two. In alternative embodiments, other aliphatic or aromatic spacer groups (L) can be employed for $(CH_2)_n$.

$R^{50}$ and $R^{51}$ are each independently —H, an aliphatic group, a substituted aliphatic group, an aminoalkyl group, —$NR^3R^4$, an aromatic group, a substituted aromatic group, a benzyl group, a substituted benzyl group, a non-aromatic heterocyclic group, a substituted non-aromatic heterocyclic group or a covalent bond between the nitrogen atom an adjacent carbon atom.

$R^3$ and $R^4$ are independently —H, an acyl group, a substituted acyl group, an aliphatic group, a substituted aliphatic group, an aromatic group, a substituted aromatic group, a benzyl group, a substituted benzyl group, a non-aromatic heterocyclic group or a substituted non-aromatic heterocyclic group.

$R^3$ and $R^4$ taken together with the atom to which they are bonded, can alternatively form a substituted or unsubstituted non-aromatic carbocyclic or heterocyclic ring.

In a preferred embodiment $R^{50}$ is a substituted aliphatic group, such as a substituted $C_1$ to about $C_{12}$ alkyl group, and $R^5s$ is —H or a substitited or unsubstituted aliphatic group. More preferably, $R^{50}$ is a substituted linear or branched $C_2$ to about $C_7$ aliphatic group wherein one or more carbon atoms can be replaced by a heteroatom, such as nitrogen, oxygen or sulfur, and $R^{51}$ is —H or a linear or branched $C_1$ to about $C_6$ or a $C_1$ to about $C_3$ aliphatic group wherein one or more carbon atoms can be replaced by a heteroatom. $R^{50}$ and $R^{50}$ can be substituted with one or more suitable substituents, as described herein, preferably with an aromatic group (e.g., phenyl, 4-halophenyl). For example, $R^{50}$ can be selected from the group consisting of:

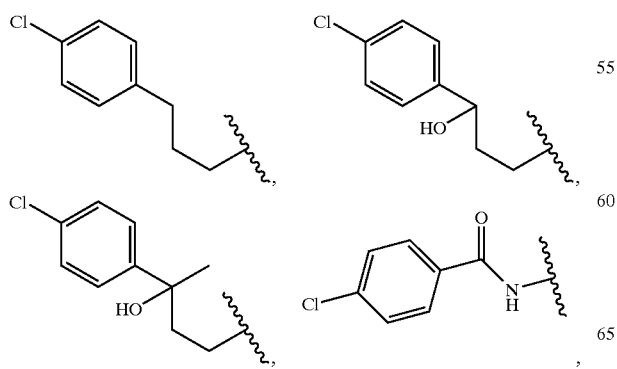

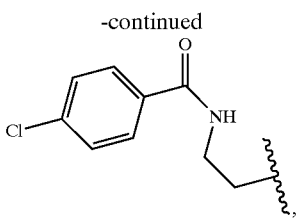

The activity of chemokine receptor antagonists represented by Structural Formula IX can be affected by the character of the nitrogen atom to which $R^{50}$ and $R^{51}$ are bonded. It is believed that compounds in which said nitrogen atom is basic can have potent chemokine receptor antagonist activity. It is known that the basicity of a nitrogen atom can be decreased when the nitrogen atom is bonded to a carbonyl group, sulfonyl group or a sulfinyl group. Therefore, it is preferred that neither $R^{50}$ nor $R^{51}$ comprise a carbonyl group, sulfonyl group or sulfinyl group that is directly bonded to the nitrogen atom.

In another aspect, the antagonist of chemokine receptor function is represented by Structural Formula (VII):

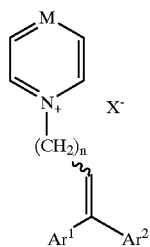

(VII)

and physiologically acceptable salts thereof.

Ar¹ and Ar² are as described in Structural Formula (I).

n is an integer, such as an integer from one to about four. Preferably, n is one, two or three. More preferably n is two. In alternative embodiments, other aliphatic or aromatic spacer groups (L) can be employed for $(CH_2)_n$.

M is >$NR^2$ or >$CR^2$.

$R^2$ is —H, —OH, an acyl group, a substituted acyl group, —$NR^5R^6$, an aliphatic group, a substituted aliphatic group, an aromatic group, a substituted aromatic group, a benzyl group, a substituted benzyl group, a non-aromatic heterocyclic group, a substituted non-aromatic heterocyclic group, —O-(substituted or unsubstituted aromatic group) or —O-(substituted or unsubstituted aliphatic group). $R^2$ is preferably an aromatic group or a substituted aromatic group.

$R^5$ and $R^6$ are independently —H, an acyl group, a substituted acyl group, an aliphatic group, a substituted aliphatic group, an aromatic group, a substituted aromatic group, a benzyl group, a substituted benzyl group, a non-aromatic heterocyclic group or a substituted non-aromatic heterocyclic group.

R⁵ and R⁶ taken together with the atom to which they are bonded, can alternatively form a substituted or unsubstituted non-aromatic carbocyclic or heterocyclic ring.

X⁻ is a physiologically acceptable anion. Preferably, X⁻ is Cl⁻ or Br⁻.

The chemokine receptor antagonist described herein can be prepared and administered as active compounds or as prodrugs. Generally, prodrugs are analogues of pharmaceutical agents which can undergo chemical conversion by metabolic processes to become fully active. For example, A prodrug of the invention can be prepared by selecting appropriate groups for $R^{40}$. In one embodiment, a prodrug can be represented by Structural Formula (VIII):

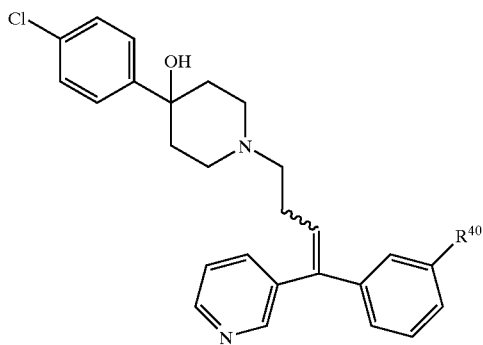

(VIII)

wherein, $R^{40}$ is Q-substituted aliphatic group, and the aliphatic group is substituted with $—(O)_u—(CH_2)_t—C(O)OR^{20}$, wherein Q is $—C(O)O—$, u is one, t is zero and $R^{20}$ is a cyclic aliphatic group. For example, when the substituted aliphatic group is a substituted ethyl group, $R^{40}$ can be represented by:

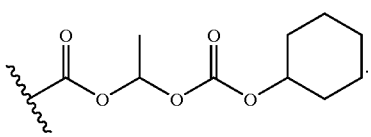

Such a prodrug can be converted to an active chemokine receptor antagonist represented by Structural Formula (VIII), wherein $R^{40}$ is —COOH.

Another embodiment provides novel compounds employed in these methods.

The double bond-containing compounds disclosed herein can be obtained as E- and Z-configurational isomers. It is expressly pointed out that the invention includes compounds of the E-configuration and the Z-configuration around the double bond, and a method of treating a subject with compounds of the E-configuration, the Z-configuration, and mixtures thereof. Accordingly, in the structural formulas presented herein, the symbol:

is used to represent both E-configuration and the Z-configuration. Preferably Ar¹ and the $(CH_2)_n$ moiety are in the cis configuration. For example, the compounds can have the configuration of:

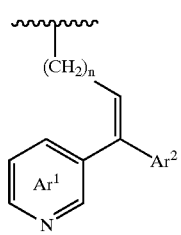

It is understood that one configuration can have greater activity than another. The desired configuration an be determined by screening for activity, employing the methods described herein.

Additionally, certain compounds of the invention may be obtained as different sterioisomers (e.g., diastereomers and enantiomers). It is pointed out that the invention includes all isomeric forms and racemic mixtures of the disclosed compounds and a method of treating a subject with both pure isomers and mixtures thereof, including racemic mixtures. Again, it is understood that one sterioisomer may be more active than another. The desired isomer can be determined by screening.

Also included in the present invention are physiologically acceptable salts of the compounds represented by Structural Formulas (I) through (VIII). Salts of compounds containing an amine or other basic group can be obtained, for example, by reacting with a suitable organic or inorganic acid, such as hydrogen chloride, hydrogen bromide, acetic acid, citric acid, perchloric acid and the like. Compounds with a quaternary ammonium group also contain a counteranion such as chloride, bromide, iodide, acetate, perchlorate and the like. Salts of compounds containing a carboxylic acid or other acidic functional group can be prepared by reacting with a suitable base, for example, a hydroxide base. Salts of acidic functional groups contain a countercation such as sodium, potassium, ammonium, calcium and the like.

As used herein, aliphatic groups include straight chained, branched or cyclic $C_1$–$C_{20}$ hydrocarbons which are completely saturated or which contain one or more units of unsaturation. Preferred aliphatic groups are $C_1$ to about $C_{10}$ hydrocarbons. More preferred are $C_1$ to about $C_6$ or $C_1$ to about $C_3$ hydrocarbons. One or more carbon atoms in an aliphatic group can be replaced with a heteroatom, such as nitrogen, oxygen or sulfur. For example, suitable aliphatic groups include substituted or unsubstituted linear, branched or cyclic $C_1$–$C_{20}$ alkyl, alkenyl or alkynyl groups.

An aminoalkyl group is an alkyl group substituted with —NR²⁴R²⁵, R²⁴ and R²⁵ are as described herein. Preferably the alkyl moiety comprises one to about twelve, more preferably one to about six carbon atoms. The alkyl moiety of an aminoalkyl group can be unsubstituted or substituted as described herein for aliphatic groups. Examples of suitable aminoalkyl groups include aminomethyl, 2-aminoethyl, 3-aminopropyl, 4-aminobutyl, dimethylaminoethyl, diethylaminomethyl, methylaminohexyl, aminoethylenyl and the like.

Aromatic groups include carbocyclic aromatic groups such as phenyl, 1-naphthyl, 2-naphthyl, 1-anthracyl and 2-anthracyl, and heterocyclic aromatic or heteroaryl groups such as N-imidazolyl, 2-imidazolyl, 4-imidazolyl, 5-imidazolyl, 2-thienyl, 3-thienyl, 2-furanyl, 3-furanyl, 2-pyrrolyl, 3-pyrrolyl, 2-pyridyl, 3-pyridyl, 4-pyridyl, 2-pyrimidyl, 4-pyrimidyl, 5-pyrimidyl, 3-pyridazinyl, 4-pyridazinyl, 3-pyrazolyl, 4-pyrazolyl, 5-pyrazolyl, 2-pyrazinyl, 2-thiazolyl, 4-thiazolyl, 5-thiazolyl, 5-tetrazolyl, 2-oxazolyl, 4-oxazolyl and 5-oxazolyl. Where these rings are fused, for example, to a non-aromatic or aromatic ring, the stated point of attachment can be either of the two fused bonds.

Aromatic groups also include fused polycyclic aromatic ring systems in which a carbocyclic aromatic ring or heteroaryl ring is fused to one or more other rings. Examples include tetrahydronaphthyl, 2-benzothienyl, 3-benzothienyl, 2-benzofuranyl, 3-benzofuranyl, 2-indolyl, 3-indolyl, 2-quinolinyl, 3-quinolinyl, 2-benzothiazolyl, 2-benzooxazolyl, 2-benzimidazolyl, 1-isoquinolinyl, 1-isoindolyl, 3-isoindolyl, acridinyl, 3-benzisoxazolyl, and the like. Also included within the scope of the term "aromatic group", as it is used herein, is a group in which one or more carbocyclic aromatic rings and/or heteroaryl rings are fused to a cycloalkyl or non-aromatic heterocyclic ring.

The term "non-aromatic ring" includes non-aromatic carbocyclic rings and non-aromatic heterocyclic rings. Non-aromatic heterocyclic rings are non-aromatic carbocyclic rings which include one or more heteroatoms such as nitrogen, oxygen or sulfur in the ring. The ring can be five, six, seven or eight-membered and/or fused to another ring, such as a cycloalkyl on aromatic ring. Examples of non-aromatic rings include, for example, 1,3-dioxolan-2-yl, 3-1H-benzimidazol-2-one, 3-1-alkyl-benzimidazol-2-one, 3-1-methyl-benzimidazol-2-one, 2-tetrahydrofuranyl, 3-tetrahydrofuranyl, 2-tetrahyrothiophenyl, 3-tetrahyrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidyl, 1–3-alkyl-phthalimidyl, tetrahydronapthyl, benzocyclopentane, benzocyclohexane, benzoxane, benzopyrolidine, benzopiperidine, benzoxolane, benzothiolane, benzothiane,

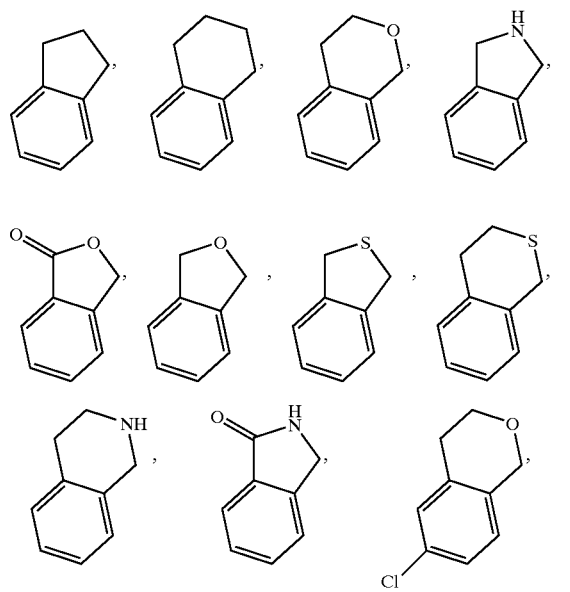

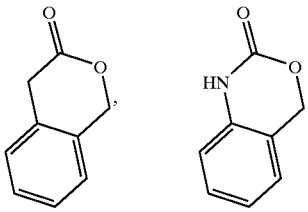

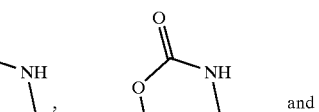

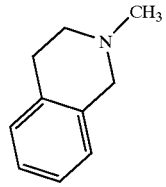

Suitable substituents on an aliphatic group, aromatic group (carbocyclic and heteroaryl), non-aromatic heterocyclic ring or benzyl group include, for example, an electron withdrawing group, a halogen, azido, —CN, —COOH, —OH, —CONR$^{24}$R$^{25}$, —NR$^{24}$R$^{25}$, —OS(O)$_2$NR$^{24}$R$^{25}$, —S(O)$_2$NR$^{24}$R$^{25}$, —SO$_3$H, —S(O)$_2$NH$_2$, guanidino, —(O)$_u$—(CH$_2$)$_t$—C(O)OR$^{20}$, —(O)$_u$—(CH$_2$)$_t$—OC(O)R$^{20}$, —(O)$_u$—(CH$_2$)$_t$—C(O)—NR$^{21}$R$^{22}$, —(O)$_u$—(CH$_2$)$_t$—NHC(O)O—R$^{20}$, —Q—H, —Q-(aliphatic group), —Q-(substituted aliphatic group), —Q-(aryl), —Q-(aromatic group), —Q-(substituted aromatic group), —Q-(CH$_2$)$_p$-(substituted or unsubstituted aromatic group) (p is an integer from 1–5), —Q-(non-aromatic heterocyclic group) or —Q-(CH$_2$)$_p$-(non-aromatic heterocyclic group).

R$^{20}$, R$^{21}$ or R$^{22}$ are independently —H, an aliphatic group, a substituted aliphatic group, an aromatic group, a substituted aromatic group, a non-aromatic heterocyclic group, —NHC(O)—O-(aliphatic group), —NHC(O)—O-(aromatic group) or —NHC(O)—O-(non-aromatic heterocyclic group) and wherein R$^{21}$ and R$^{22}$, taken together with the nitrogen atom to which they are bonded, can form a non-aromatic heterocyclic ring.

t is an integer from zero to about three, and the methylene group, —(CH$_2$)$_t$—, can be substituted, as described herein for aliphatic groups, or unsubstituted.

u is zero or one.

Q is —O—, —S—, —S(O)—, —S(O)$_2$—, —OS(O)$_2$—, —C(O)—, —OC(O)—, —C(O)O—, —C(O)C(O)—O—, —O—C(O)C(O)—, —C(O)NH—, —NHC(O)—, —OC(O)NH—, —NHC(O)O—, —NH—C(O)—NH—, —S(O)$_2$NH—, —NHS(O)$_2$—, —N(R$^{23}$)—, —C(NR$^{23}$)NHNH—, —NHNHC(NR$^{23}$)—, —NR$^{24}$C(O)— or —NR$^{24}$S(O)$_2$—.

R$^{23}$ is —H, an aliphatic group, a benzyl group, an aryl group or non-aromatic heterocyclic group.

R$^{24}$ and R$^{25}$ are independently —H, —OH, an aliphatic group, a substituted aliphatic group, a benzyl group, an aryl group or non-aromatic heterocyclic group or $R^{24}$ and $R^{25}$ taken together with the nitrogen atom to which they are bonded can form a substituted or unsubstituted non-aromatic heterocyclic ring.

A substituted non-aromatic heterocyclic ring, benzyl group or aromatic group can also have an aromatic group, an aliphatic or substituted aliphatic group as a substituent. When a non-aromatic ring (carbocyclic or heterocyclic) or an aromatic ring (carbocyclic aromatic or heteroaryl) is substituted with another ring, the two rings can be fused. substituted aliphatic group can also have an oxo group, epoxy group, non-aromatic heterocyclic ring, benzyl group, substituted benzyl group, aromatic group or substituted aromatic group as a substituent. A substituted non-aromatic heterocyclic ring can also have =O, =S, =NH or =N(aliphatic, aromatic or substituted aromatic group) as a substituent. A substituted aliphatic, substituted aromatic, substituted non-aromatic heterocyclic ring or substituted benzyl group can have more than one substituent, which can be the same or different.

Acyl groups include substituted and unsubstituted aliphatic carbonyl, aromatic carbonyl, aliphatic sulfonyl and aromatic sulfonyl.

Suitable electron withdrawing groups include, for example, alkylimines, alkylsulfonyl, carboxamido, carboxylic alkyl esters, —CH=NH, —CN, —NO$_2$ and halogens.

A "subject" is preferably a bird or mammal, such as a human, but can also be an animal in need of veterinary treatment, e.g., domestic animals (e.g., dogs, cats, and the like), farm animals (e.g., cows, sheep, fowl, pigs, horses, and the like) and laboratory animals (e.g., rats, mice, guinea pigs, and the like).

An "effective amount" of a compound is an amount which results in the inhibition of one or more processes mediated by the binding of a chemokine to a receptor in a subject with a disease associated with aberrant leukocyte recruitment and/or activation. Examples of such processes include leukocyte migration, integrin activation, transient increases in the concentration of intracellular free calcium $[Ca^{2+}]_i$ and granule release of proinflammatory mediators. Alternatively, an "effective amount" of a compound is a quantity sufficient to achieve a desired therapeutic and/or prophylactic effect, such as an amount which results in the prevention of or a decrease in the symptoms associated with a disease associated with aberrant leukocyte recruitment and/or activation.

The amount of compound administered to the individual will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. Typically, an effective amount of the compound can range from about 0.1 mg per day to about 100 mg per day for an adult. Preferably, the dosage ranges from about 1 mg per day to about 100 mg per day. An antagonist of chemokine receptor function can also be administered in combination with one or more additional therapeutic agents, e.g. theophylline, β-adrenergic bronchodilators, corticosteroids, antihistamines, antiallergic agents, immunosuppressive agents (e.g., cyclosporin A, FK-506, prednisone, methylprednisolone) and the like.

The compound can be administered by any suitable route, including, for example, orally in capsules, suspensions or tablets or by parenteral administration. Parenteral administration can include, for example, systemic. administration, such as by intramuscular, intravenous, subcutaneous, or intraperitoneal injection. The compound an also be administered orally (e.g., dietary), transdermally, topically, by inhalation (e.g., intrabronchial, intranasal, oral inhalation or intranasal drops), or rectally, depending on the disease or condition to be treated. Oral or parenteral administration are preferred modes of administration.

The compound can be administered to the individual in conjunction with an acceptable pharmaceutical or physiological carrier as part of a pharmaceutical composition for treatment of HIV infection, inflammatory disease, or the other diseases discussed above. Formulation of a compound to be administered will vary according to the route of administration selected (e.g., solution, emulsion, capsule). Suitable carriers may contain inert ingredients which do not interact with the compound. Standard pharmaceutical formulation techniques can be employed, such as those described in Remington's Pharmaceutical Sciences, Mack Publishing Company, Easton, Pa. Suitable carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986).

The activity of compounds of the present invention can be assessed using suitable assays, such as receptor binding assays and chemotaxis assays. For example, as described in the Exemplification Section, small molecule antagonists of RANTES and MIP-1α binding have been identified utilizing THP-1 cells which bind RANTES and chemotax in response to RANTES and MIP-1α as a model for leukocyte chemotaxis. Specifically, a high through-put receptor binding assay, which monitors $^{125}$I-RANTES and $^{125}$I-MIP-1α binding to THP-1 cell membranes, was used to identify small molecule antagonists which block binding of RANTES and MIP-1α. Compounds of the present invention can also be identified by virtue of their ability to inhibit the activation steps triggered by binding of a chemokine to its receptor, such as chemotaxis, integrin activation and granule mediator release. They can also be identified by virtue of their ability to block RANTES and MIP-1α mediated HL-60, T-cell, peripheral blood mononuclear cell, and eosinophil chemotactic response.

The compounds disclosed herein can be prepared accordingly to the schemes shown in FIGS. 1–5 and 7. The schemes are described in greater detail below.

FIG. 1 shows the preparation of compounds represented by Structural Formula (I). $L^1$ is PPh$_3$Cl, PPh$_3$Br, PPh$_3$I or (EtO)$_2$P(O), $L^2$ is a suitable leaving group such as halogen, p-toluene sulfonate, mesylate, alkoxy, and phenoxy; Pg is a suitable protecting group such as tetrahydropyranyl; and the other symbols are as defined above.

In Step 1 of FIG. 1, a Wittig reaction is carried out in a solvent such as ether, or tetrahydrofuran (THF) in the presence of a base such as sodium hydride, n-butyl lithium or lithium diisopropylamide (LDA) at 0° C. up to the reflux temperature for the solvent used for 5 minutes to 72 h. Compounds represented by Formula II in FIG. 1 can be prepared by methods disclosed in J. Med. Chem., 1992 (35) 2074–2084, the entire teachings of which are incorporated herein by reference.

In Step 2 of FIG. 1, deprotection is carried out with an acid in a solvent such as methanol at room temperature up to the reflux temperature for the solvent used for 5 minutes to 72 h. Alternatively, a compound of represented by Formula V in FIG. 1 can be prepared directly from step 1 without isolating an intermediate. The reaction mixture obtained after the work up of the reaction described in step 1 can be dissolved in the solvent and reacted with the acid.

In Step 3 of FIG. 1, the hydroxy group can be converted to a leaving group by known methods. Compounds represented by Formula VI in FIG. 1 can be prepared by methods disclosed in J. Med. Chem., 1992 (35) 2074–2084 and J. Org. Chem., 1977 (42) 353.

In Step 4 of FIG. 1, an alkylation reaction is carried out in a solvent such as acetone, methyl ethyl ketone, ethyl acetate, toluene, tetrahydrofuran (THF) or dimethylformamide (DMF) in the presence of a base such as potassium carbonate or sodium hydride and a catalyst such as an alkali metal iodide at room temperature up to the reflux temperature for the solvent used for 5 minutes to 72 h.

Figure 2:
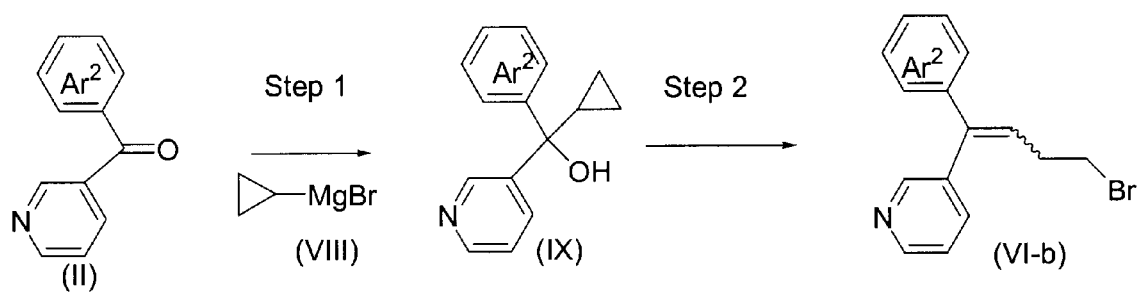
FIG. 2 is a schematic showing the preparation of the compounds represented by Compound (VI-b).

FIG. 2 shows the preparation of compounds represented by Compound (VI-b). In Step 1 of FIG. 2, a Grignard reaction may be carried out in a solvent such as ether, or tetrahydrofuran (THF) at 0° C. up to the reflux temperature for the solvent used for 5 minuets to 72 h. Compound VII is available commercially.

In Step 2 of FIG. 2, bromination may be carried out with brominate agents such as hydrobromic acid, bromotrimethylsilane or boron tribromide-methyl sulfide complex in a solvent such as acetic acid, dichloromethane or dichloroethane at room temperature up to the reflux temperature for the solvent used for 5 minutes to 72 h.

Figure 3:
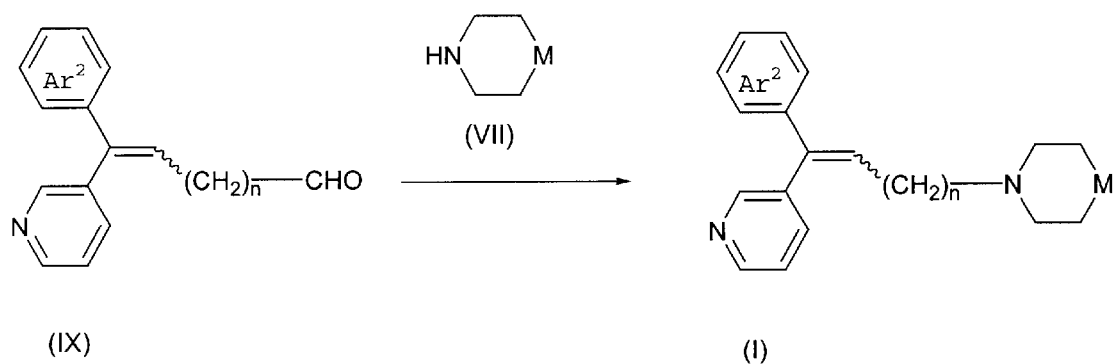
FIG. 3 is a schematic showing the preparation of the compounds represented by Structural Formula (I)

FIG. 3 shows the preparation of compounds represented by Structural Formula (I). In FIG. 3, a reductive amination may be carried out with reducing regents such as sodium cyanoborohydride, sodium acetoxyborohydride or sodium borohydride in a solvent such as methanol, ethanol, tetrahydrofuran (THF), dichloromethane or dichloroethane at room temperature up to the reflux temperature for the solvent used for 5 minutes to 72 h.

Figure 4:
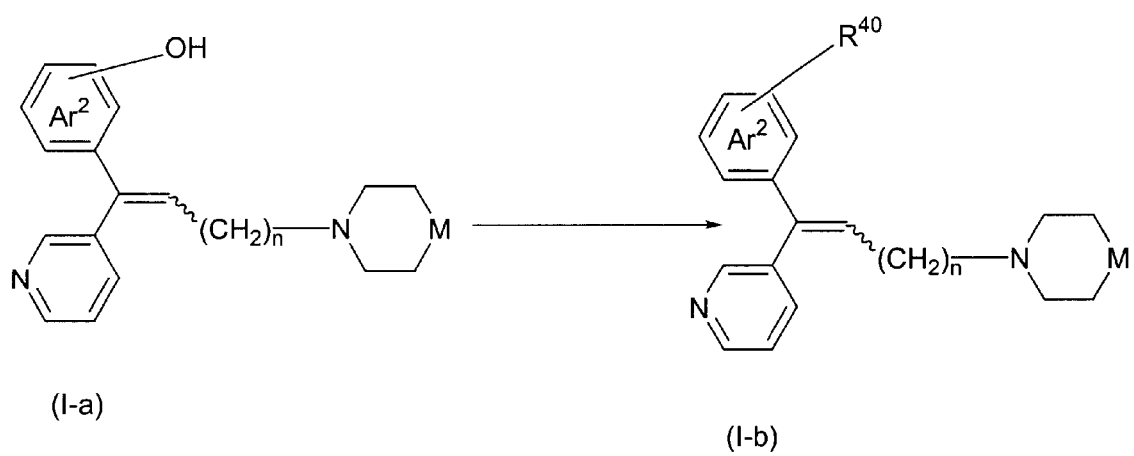
FIG. 4 is a schematic showing the preparation of representative compounds of Structural Formula (I), wherein $Ar^1$ and/or $Ar^2$ can be substituted with $R^{40}$.

FIG. 4 shows the preparation of representative compounds represented of Structural Formula (I), wherein $Ar^1$ and/or $Ar^2$ can be substituted with $R^{40}$. In FIG. 4, the alkylation reaction may be carried out in a solvent such as acetone, methyl ethyl ketone, ethyl acetate, toluene, tetrahydrofuran (THF) or dimethylformamide (DMF) in the presence of a base such as potassium carbonate or sodium hydride and a catalyst such as an alkali metal iodide at room temperature up to the reflux temperature for the solvent used for 5 minutes to 72 h.

Figure 5:
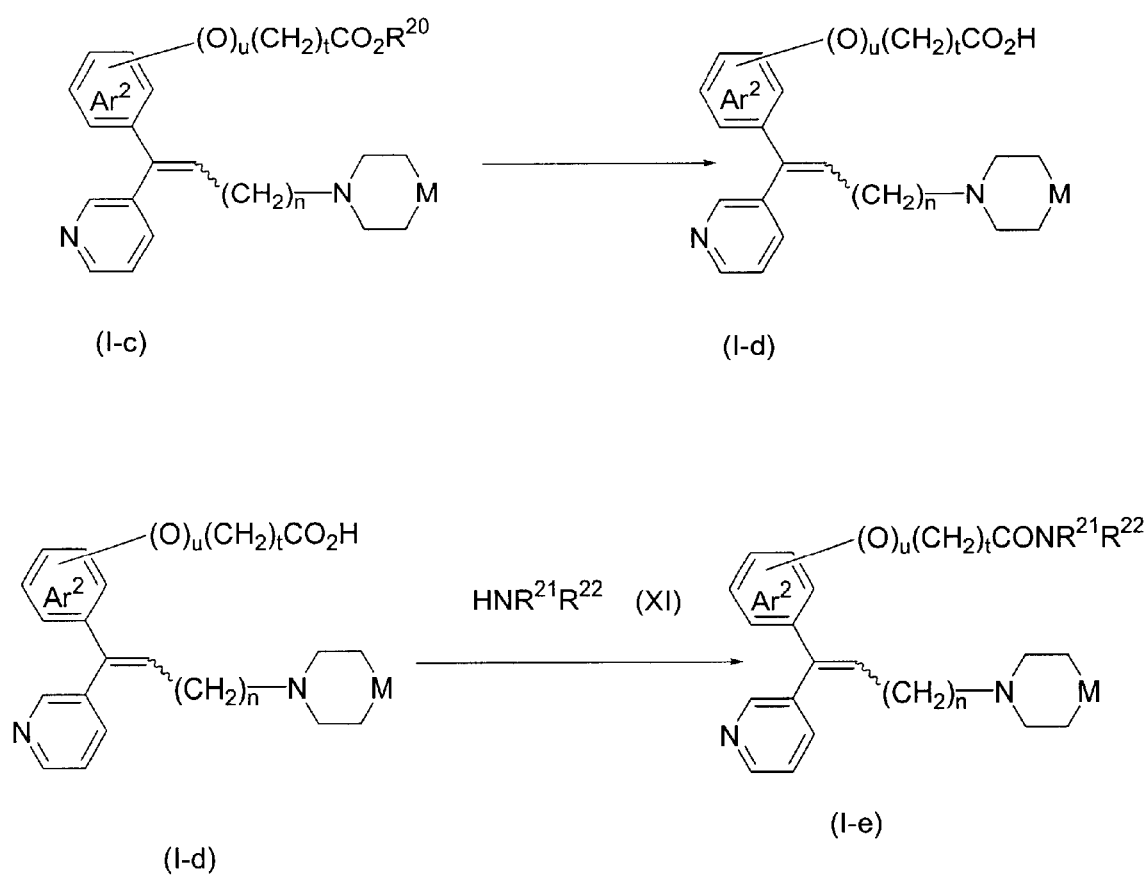
FIG. 5 is a schematic showing the preparation of representative compounds of Structural Formula (I), wherein $Ar^1$ and/or $Ar^2$ can be substituted with $-(O)_u-(CH_2)_t-COOR^{20}$, $-(O)_u-(CH_2)_t-OC(O)R^{20}$, $-(O)_u-(CH_2)_t-C(O)-NR^{21}R^{22}$ or $-(O)_u-(CH_2)_t-NHC(O)O-R^{20}$.
Figure 6A:
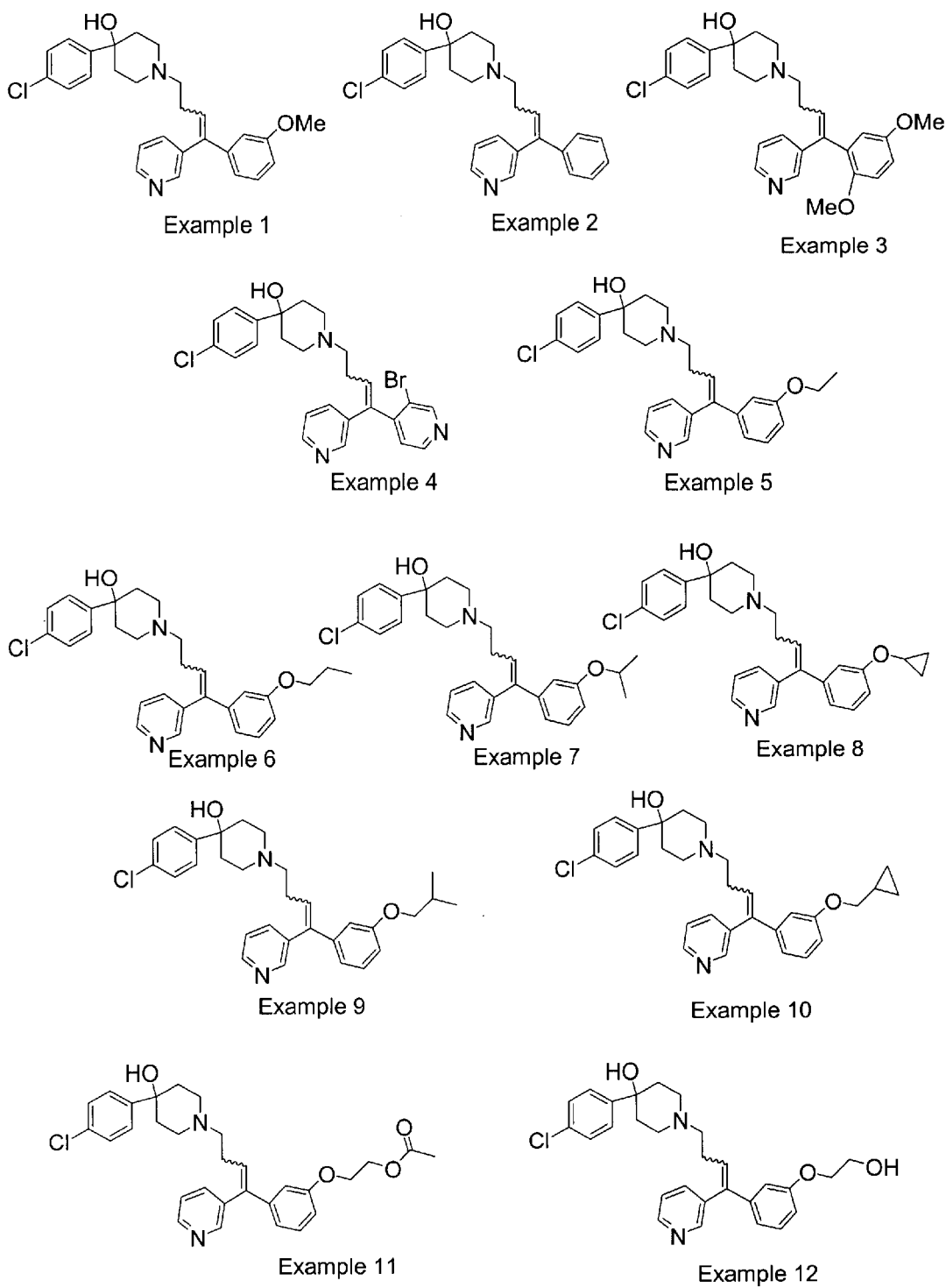
FIG. 6A–6J show the structures of exemplary compounds of the present invention.
Figure 6B:
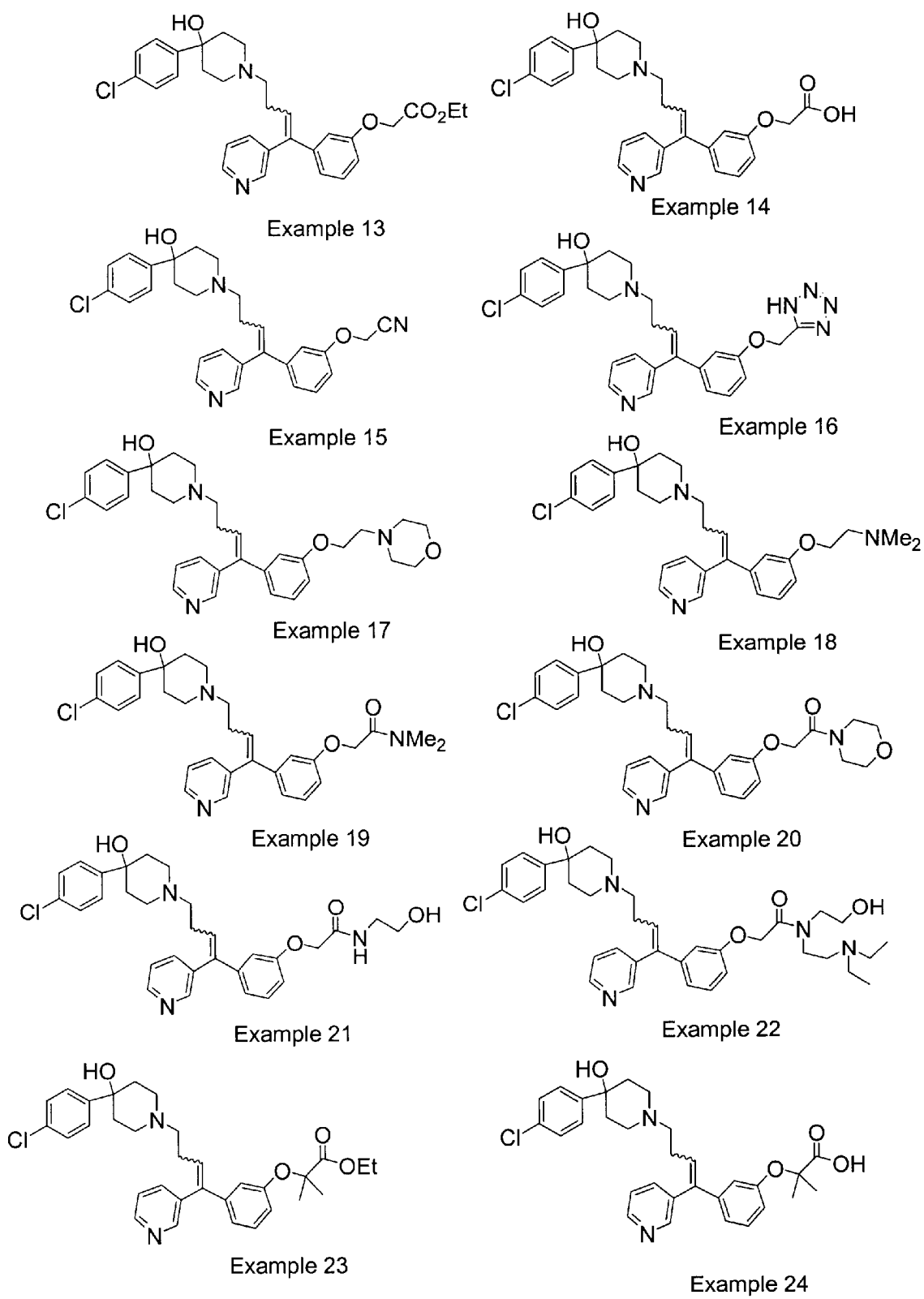
Figure 6C:
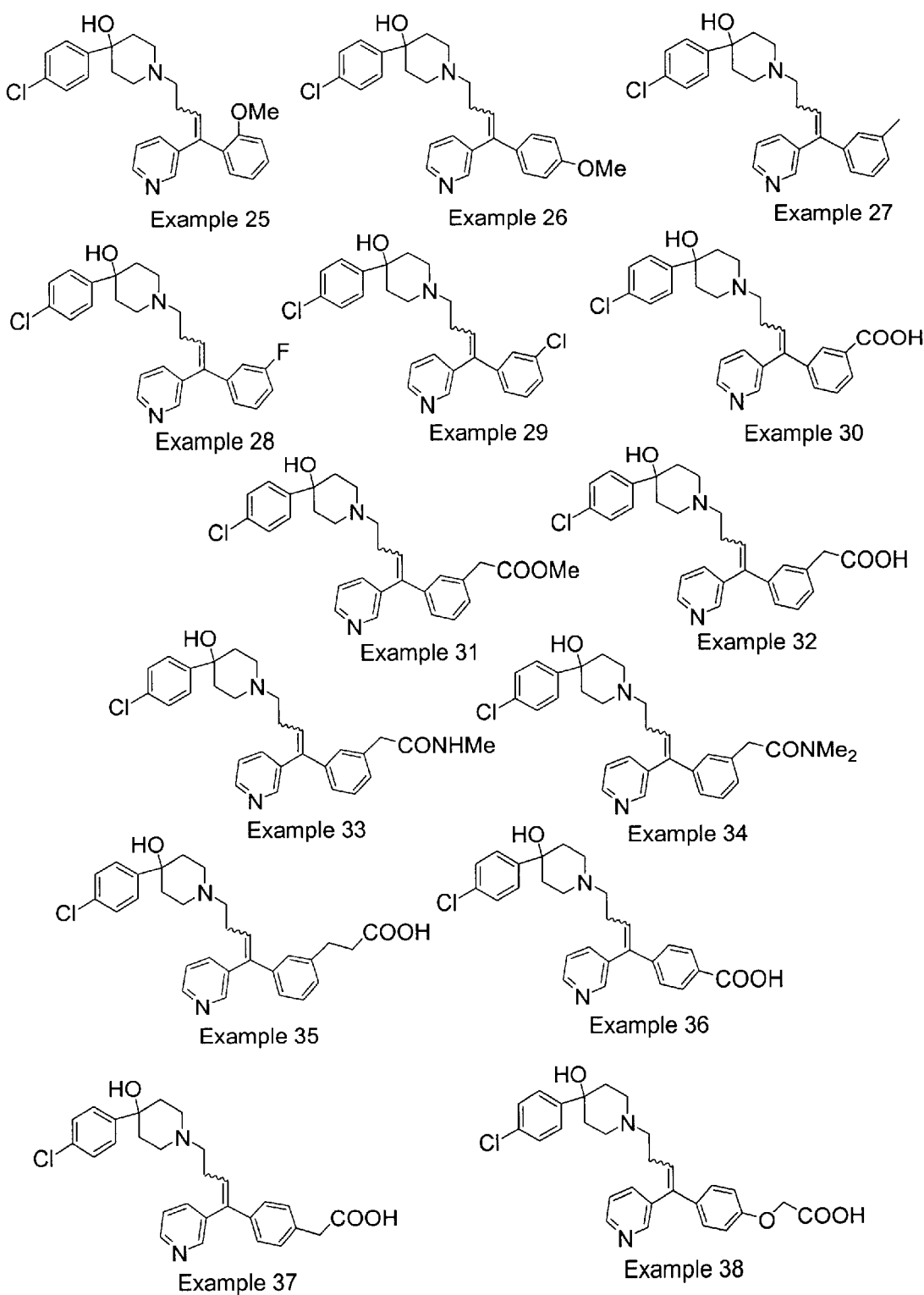
Figure 6D:
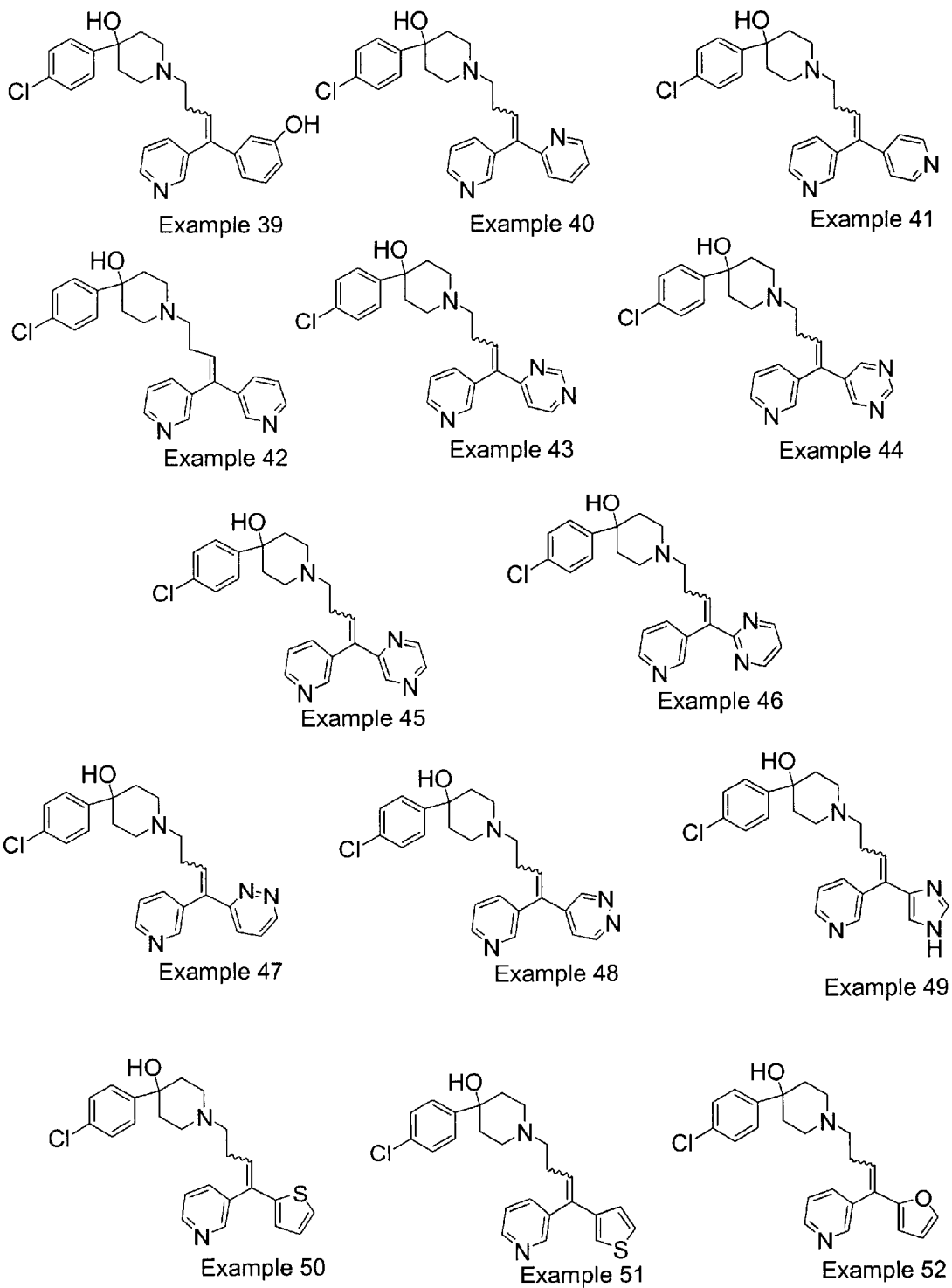
Figure 6E:
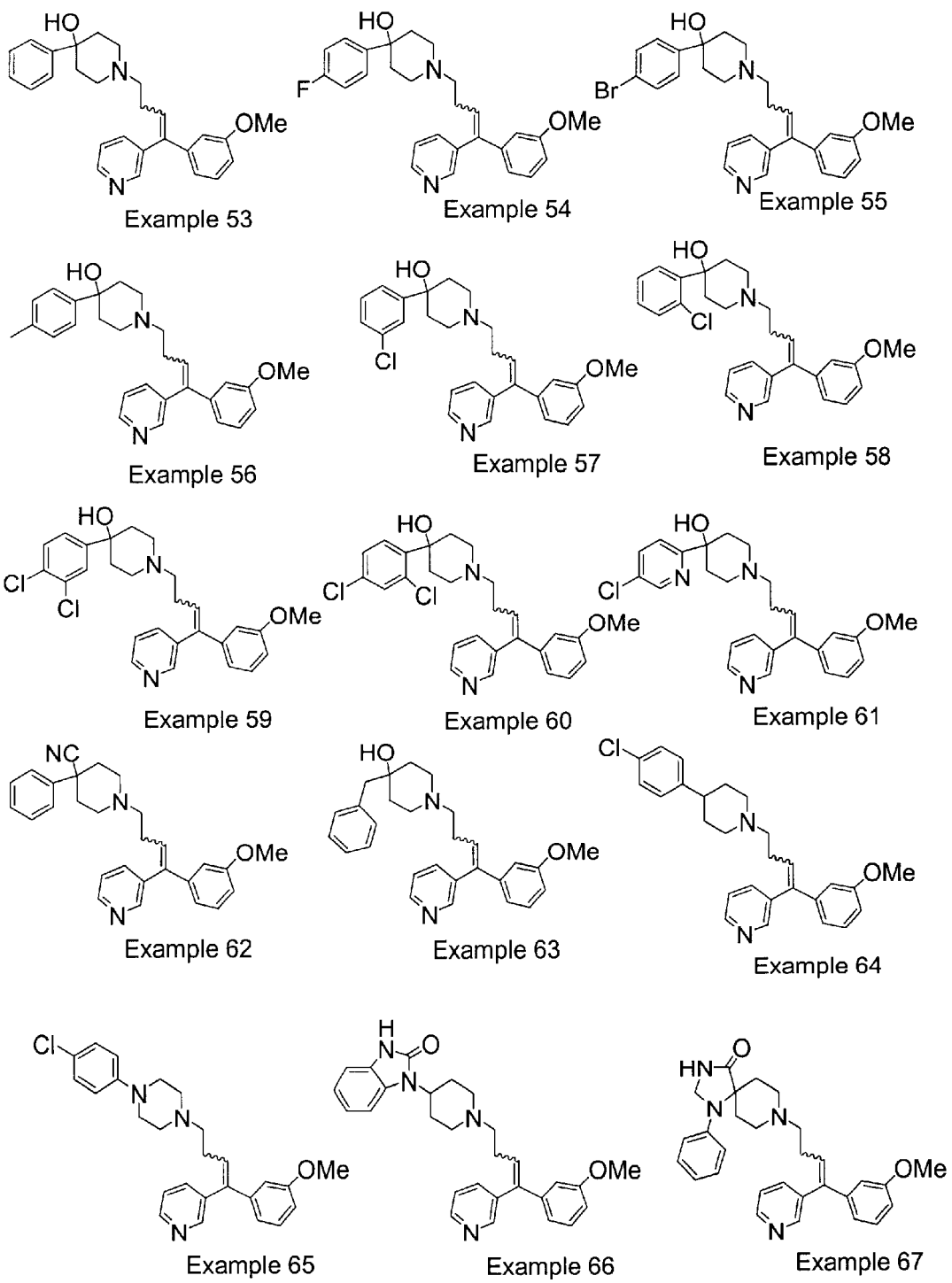
Figure 6F:
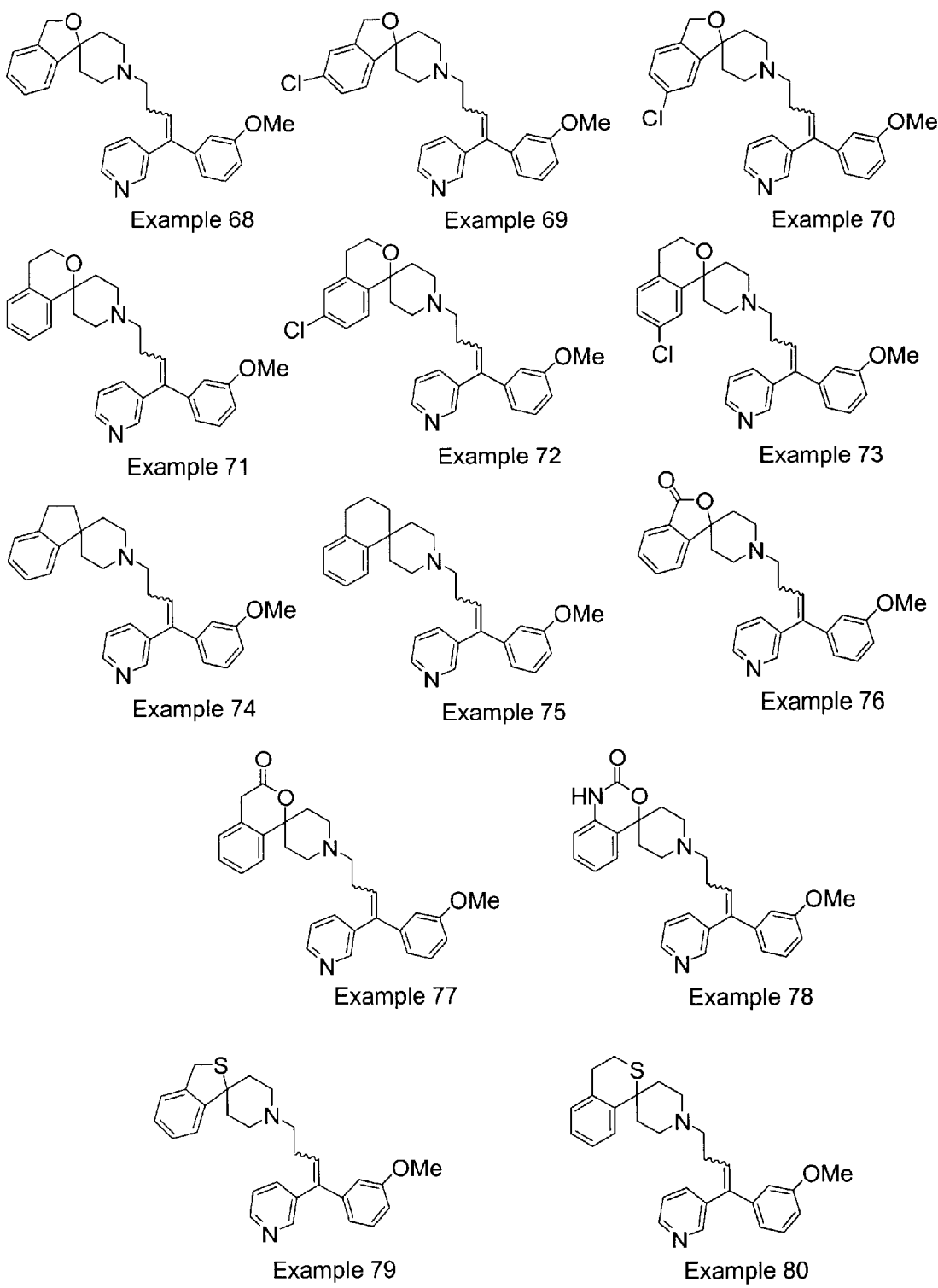
Figure 6G:
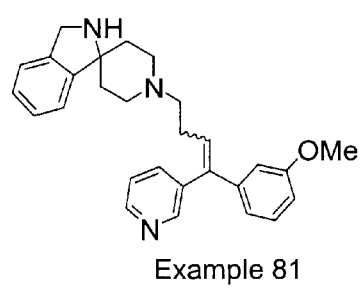
Figure 6G:
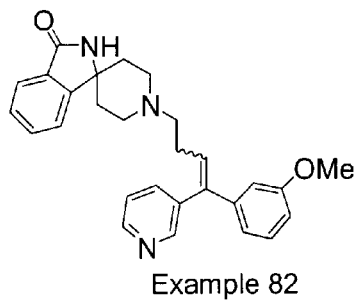
Figure 6G:
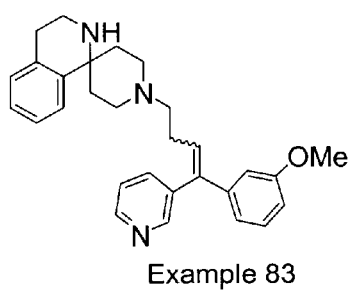
Figure 6G:
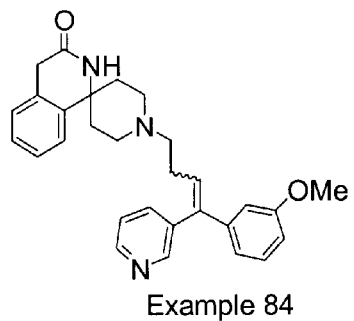
Figure 6G:
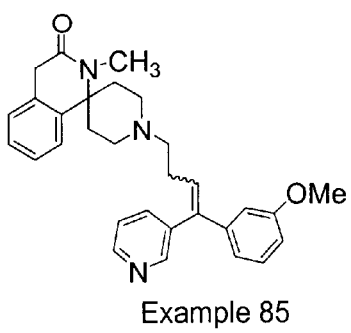
Figure 6G:
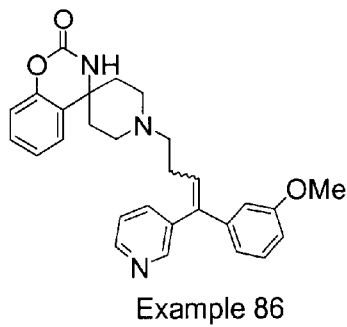
Figure 6G:
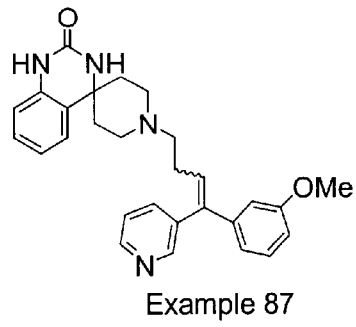
Figure 6G:
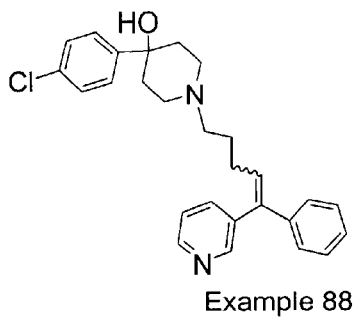
Figure 6G:
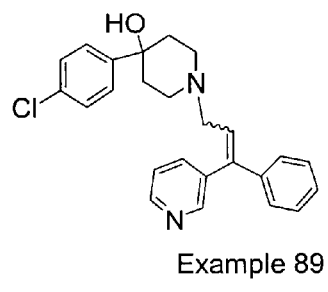
Figure 6G:
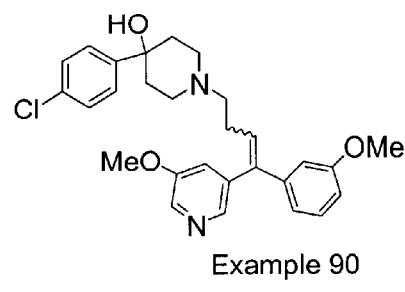
Figure 6H:
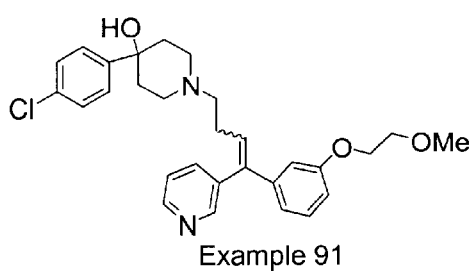
Figure 6H:
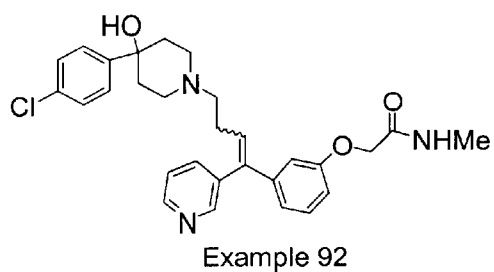
Figure 6H:
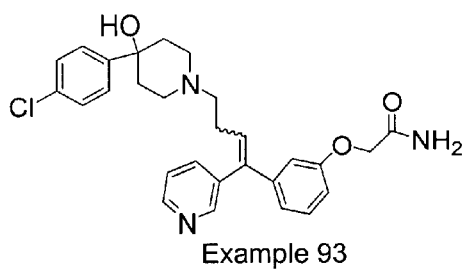
Figure 6H:
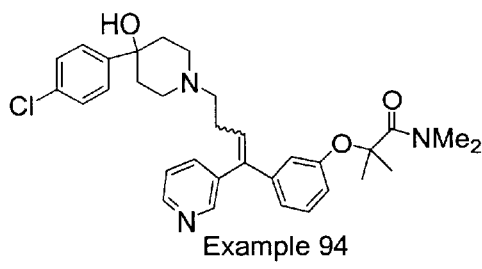
Figure 6H:
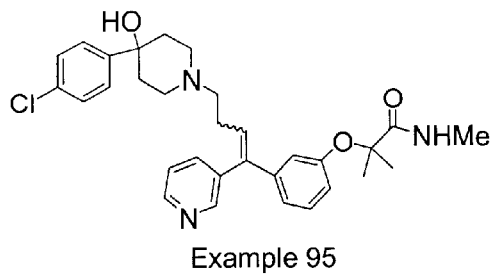
Figure 6H:
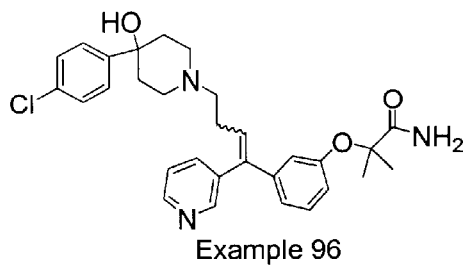
Figure 6H:
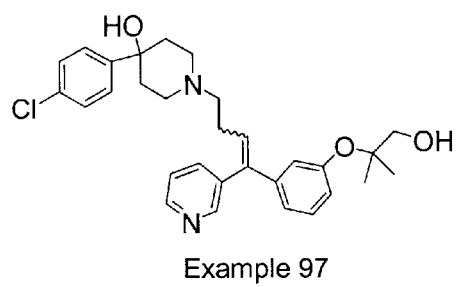
Figure 6H:
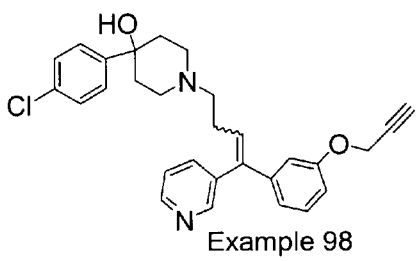
Figure 6H:
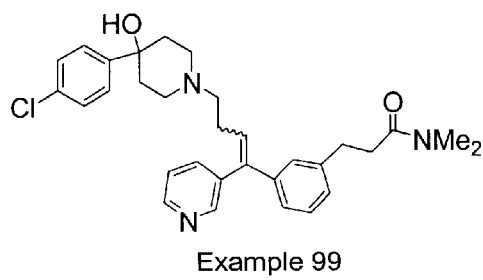
Figure 6H:
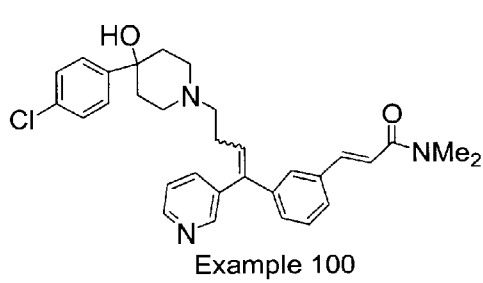
Figure 6I:
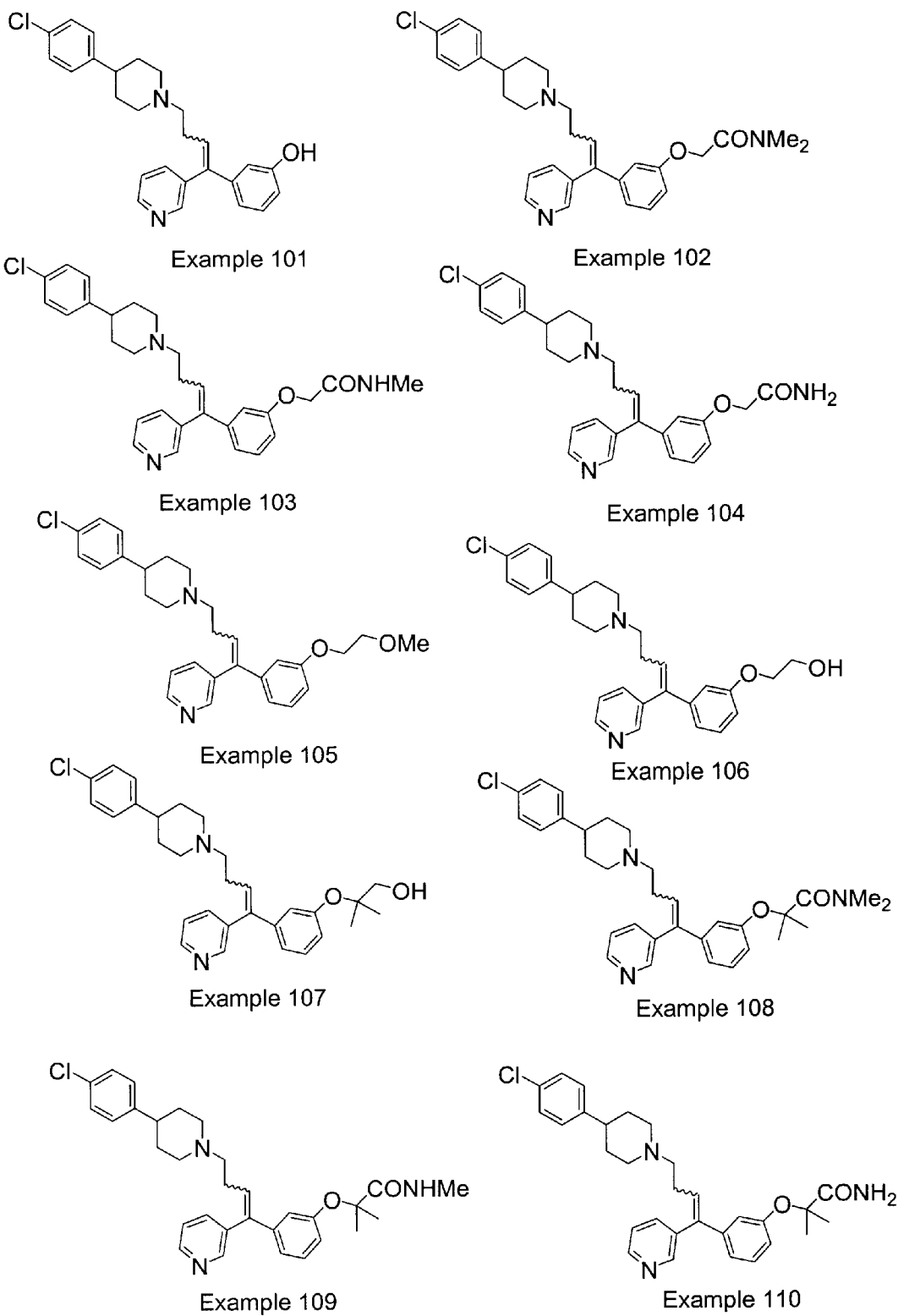
Figure 6J:
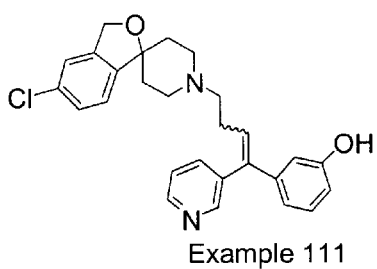
Figure 6J:
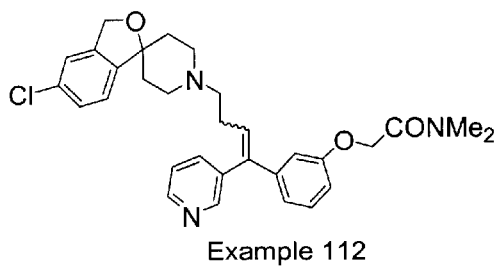
Figure 6J:
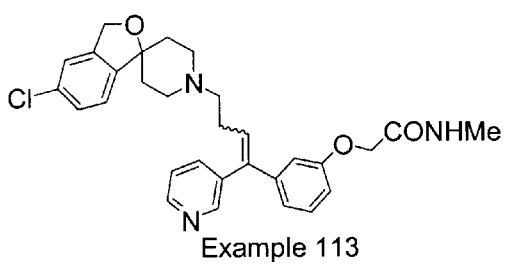
Figure 6J:
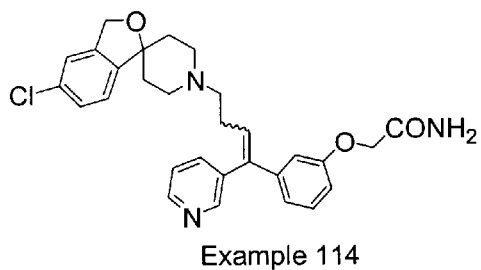
Figure 6J:
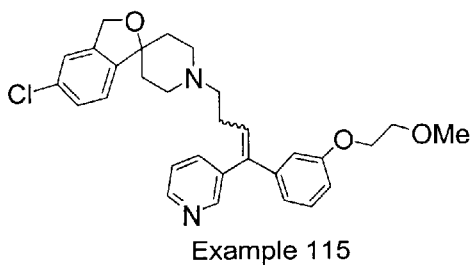
Figure 6J:
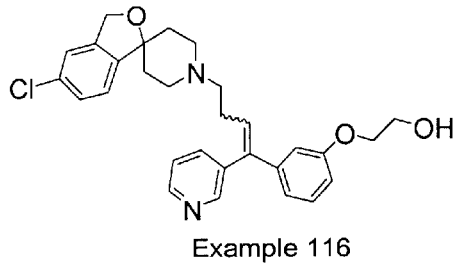
Figure 6J:
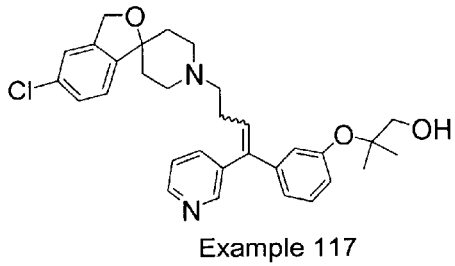
Figure 6J:
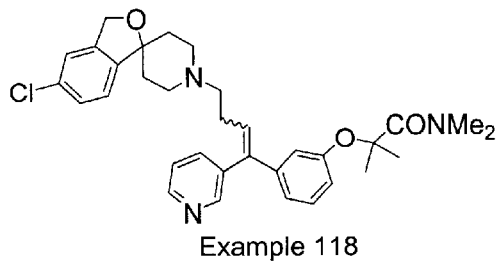
Figure 6J:
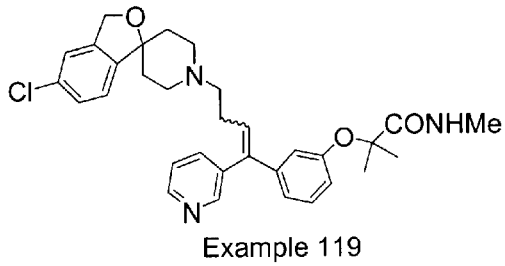
Figure 6J:
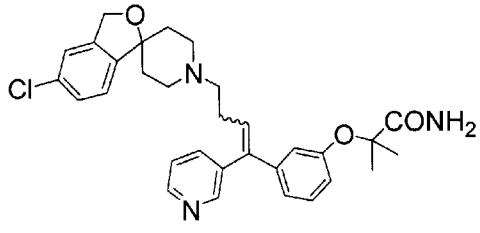

FIG. 5 is a schematic showing the preparation of representative compounds of Structural Formula (I), wherein $Ar^1$ and/or $Ar^2$ can be substituted with —$(O)_u$—$(CH_2)_t$—$COOR^{20}$, —$(O)_u$—$(CH_2)_t$—$OC(O)R^{20}$, —$(O)_u$—$(CH_2)_t$—$C(O)$—$NR^{21}R^{22}$ or —$(O)_u$—$(CH_2)_t$—$NHC(O)O$—$R^{20}$. In FIG. 5, the hydrolysis reaction may be carried out in a mixture of aqueous alkali metal hydroxide solution and a solvent such as methanol, ethanol, tetrahydrofuran (THF) or dioxane at room temperature up to the reflux temperature for the solvent used for 5 minutes to 72 h. The acylation reaction can be carried out using dicyclohexylcarbodiimide (DCC) or (1-ethyl-3-(3-dimethylaminopropyl)carbodiimide (DEC) in a solvent such as tetrahydrofuran (THF), dimethylformamide (DMF) or methylene chloride in the presence of a base such as pyridine or triethylamine (when necessary) at temperatures of 0 to 100° C. for 5 minutes to 72 h.

Figure 7:
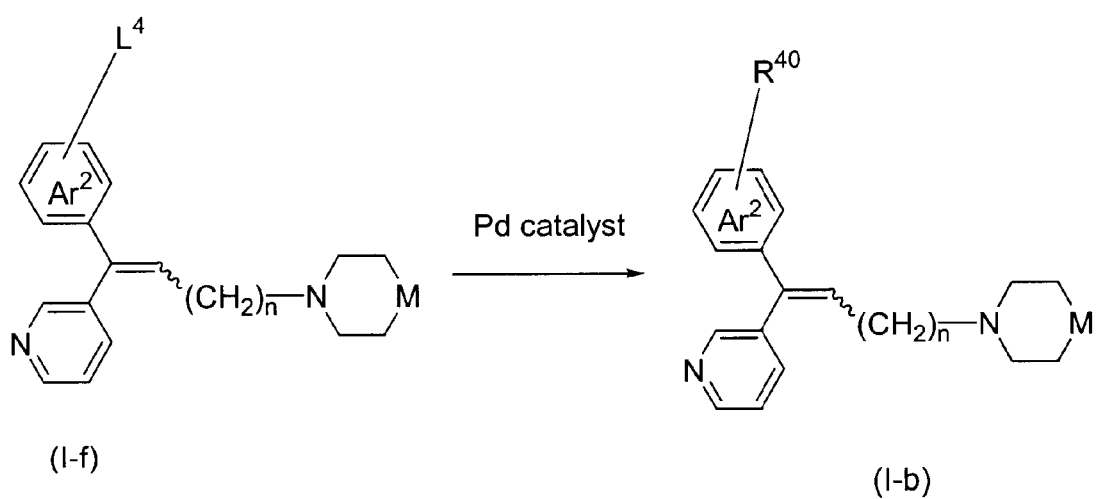
FIG. 7 shows the preparation of compounds represented by Structural Formula (I) wherein $Ar^1$ or $Ar^2$ is substituted with $R^{40}$.

FIG. 7 shows the preparation of compounds represented by Structural Formula (I) wherein $Ar^1$ or $Ar^2$ is substituted with $R^{40}$. L4 is a suitable leaving group such as halogen or trifluoromethylsulfonate. In FIG. 7, a palladium coupling reaction such as Stille coupling, Suzuki coupling, Heck reaction, or carboxylation using carbon monoxide can be carried out using a palladium catalyst such as tetrakis (triphenylphosphine)palladium, bis(triphenylphosphine) palladium chloride, and palladium acetate in a solvent such as tetrahydrofuran (THF), 1,4-dioxane, toluene, dimethylformamide (DMF), or dimethylsufoxide (DMSO) in the presence of additive (when necessary) such as triphenylphosphine, 1,1'-bis(diphenylphosphino)ferrocene, triethylamine, sodium bicarbonate, tetraethylammonium chloride, or lithium chloride at room temperature up to the reflux temperature for the solvent used for 5 minutes to 72 h.

Figure 8A:
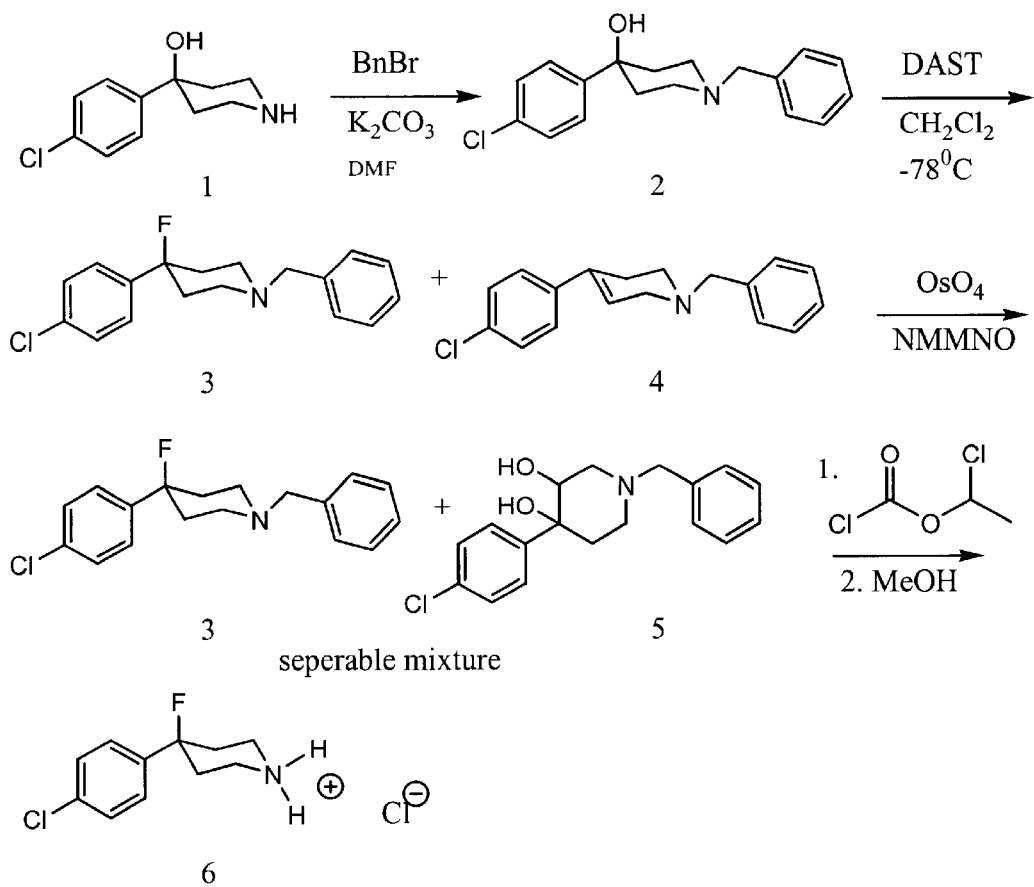
FIG. 8A is a schematic showing the preparation of 4-(4-chlorophenyl)-4-fluoropiperidine.

FIG. 8A shows the preparation of N-benzyl-4-(4-chlorophenyl)-4-hydroxypiperidine.

Step 1

To a stirred solution of commercially available 4-(4-chlorophenyl)-4-hydroxypiperidine (10 g, 47 mmol., 1) in anhydrous DMF (10 mL) was added benzyl bromide (5.6 mL, 47 mmol) and $K_2CO_3$ (7.4 g, 94 mmol.) and stirred at RT overnight. Excess solvent was removed under reduced pressure, brought up into $CH_2Cl_2$ (100 mL) washed with $H_2O$ (2×50 mL). Organic layer separated, dried over $Na_2SO_4$ and charged on a silica gel flash column. Eluting off with 2% MeOH/$CH_2Cl_2$ 10 g 2 (80% yield) was obtained as a viscous liquid. MS m/z: (M+ 303)

Step 2

N-Benzyl-4-(4-chlorophenyl)-4-fluoropiperidine

To a cold (−78° C.) solution of 2 (10 g, 33 mmol) in $CH_2Cl_2$ (20 mL) was slowly added DAST (diethylaminosulfur trifluoride, 5.3 mL, 39.8 mmol) under an inert atmosphere. The reaction was stirred at −78° C. for an additional 45 min. The reaction was quenched at −78° C. by the slow addition of enough saturated aqueous sodium bicarbonate solution to afford a pH>8. This reaction resulted a quantitative conversion of the starting material to a 1:1 mixture of fluoropiperidine 3 and 4-(4-chlorophenyl) tetrahydropyridine 4. The mixture of 3 and 4 (3.5 g, mixture, ~35% yield) was purified via silica gel flash chromatography, eluting with 2% MeOH/$CH_2Cl_2$. This mixture proved to be inseparable by silica gel flash chromatography. In order to separate out the desired product, the mixture of 3 and 4 were subjected to osmium tetroxide oxidation.

To a stirred solution of the mixture of 3 and 4 (1.8 g) in acetone/$H_2O$ (5:1, 10 mL) was added a catalytic amount of $OsO_4$ in isopropanol (2.5 mol %, 1 mL) and N-methylmorpholine-N-oxide (0.69 g, 6.56 mmol). The reaction was stirred at RT overnight. The reaction was then evaporated to dryness, brought up into $CH_2Cl_2$ and washed with $NaHSO_3$. This reaction resulted in the dihydroxylation of the undesired 4 to 5 and the clean separation of the desired fluoropiperidine 3 (1.0 g, 55% yield) from the byproduct by silica gel flash chromatography eluting with 2% MeOH/ $CH_2Cl_2$. MS m/z: (M+306)

Step 3

4-(4-Chlorophenyl)-4-fluoropiperidine

To a cold (0° C.) solution of 3 (1.07 g, 3.5 mmol) in 1,2-dichloroethane was added 1,1-chloroethylchloroformate (0.45 mL, 4.2 mmol). The reaction was then heated to reflux for 2 hrs. Excess solvent was removed and the residue was brought up into 5 mL methanol. The mixture was refluxed for 2 hrs and excess methanol was removed under reduced pressure. Precipitation of the hydrochloride salt of 6 by the addition of $CH_2Cl_2$/hexane (1:1) followed by filtration resulted in the quantitative isolation of the desired crystalline product 6 (80%, 0.70 g). MS m/z: (M+215)

The product of this scheme can be used to prepare compounds of Structural Formula (I) wherein $R^1$ is —F.

Figure 8B:
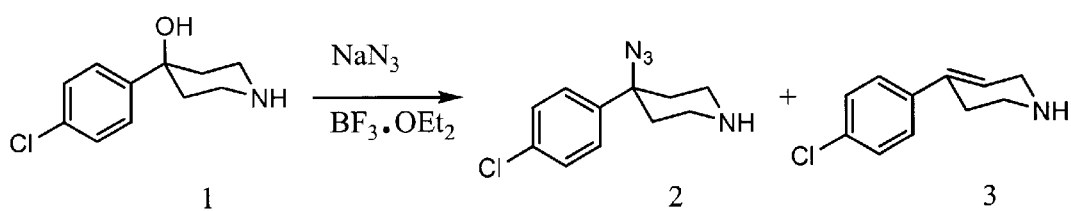
FIG. 8B is a schematic showing the preparation of 4-4-azido-4-(4-chlorophenyl)piperidine.

FIG. 8B shows the preparation of 4-azido-4-(4-chlorophenyl)piperidine.

To a cold (0° C.) solution of 1 (3.0 g, 14 mmol) in anhydrous dioxane (15 mL) under an inert atmosphere was added $NaN_3$ (1.0 g, 15.4 mmol) followed by the slow dropwise addition of and $BF_3 \cdot OEt$ (4.4 mL, 35 mmol). The reaction was stirred at 0° C. for 3 hrs and was quenched at 0° C. by the slow careful addition of saturated aqueous $NaHCO_3$ to basicity. The organic layer was separated and dried over $Na_2SO_4$. The reaction mixture was purified via silica gel flash chromatography eluting a 2 g 1:3 mixture of azidopiperidine 2 and olefin 3 with 2% $MeOH/CH_2Cl_2$. The mixture can be used directly to prepare compounds represented by Structural Formula (I) wherein $R^1$ is $-N_3$.

Figure 8C:
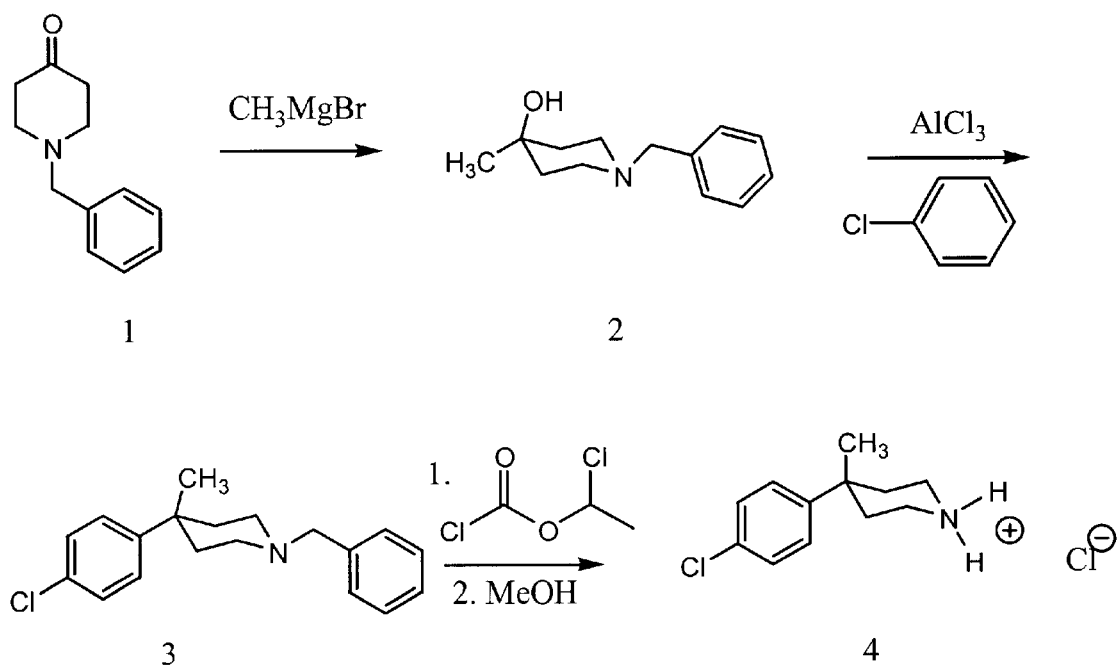
FIG. 8C is a schematic showing the preparation of 4-(4-chlorophenyl)-4-methylpiperidine.

FIG. 8C shows the preparation of N-benzyl-4-methylpiperidine.

Step 1

To a cold (−78° C.) stirred solution of 1.4 M methyllithium in THF (39 mL, 54 mmol) under an inert atmosphere was added N-benzyl-4-oxopiperidine (1, 5.1 g, 27 mmol). The reaction was stirred at −78° C. for 2 hrs. The reaction was quenched by the slow addition of saturated aqueous $NH_4Cl$, the organic layer was separated and dried over $Na_2SO_4$. Pure methylpiperidine (2) was isolated via silica gel flash chromatography eluting with 5% $MeOH/CH_2Cl_2$. MS m/z: (M+206)

Step 2

N-Benzyl-4-(4-chlorophenyl)-4-methylpiperidine:

To a flask containing chlorobenzene (10 mL, excess) and methylpiperidine (0.42 g, 2.06 mmol, 2) was added aluminum trichloride (1.65 mL, 12.4 mmol). The reaction was heated to reflux for 24 hrs. Excess chlorobenzene was removed under reduced pressure and pure 3 was obtained via silica gel flash chromatography eluting with % EtOAc/hexane. MS m/z: (M+ 300)

Step 3

4-(4-Chlorophenyl)-4-methylpiperidine: FIG. 8c

To a cold (0° C.) solution of N-benzyl-4-(4-chlorophenyl)-4-methylpiperidine (3) (0.41 g, 1.4 mmol) in $CH_2Cl_2$ was 1.1 equivalent of 1-chloroethylchloroformate. The reaction was then heated to reflux for 2 hrs. Excess solvent was removed and the residue was brought up into methanol. The mixture was refluxed for 2 hrs and excess methanol was removed under reduced pressure. Precipitation of the hydrochloride salt 4 by the addition of $CH_2Cl_2$ followed by filtration resulted in the quantitative isolation of the desired crystalline product 4 (100%, 0.34 g). MS m/z: (M+ 210)

The product of this scheme can be used to prepare compounds of Structural Formula (I) wherein $R^1$ is $-CH_3$.

Figure 9A:
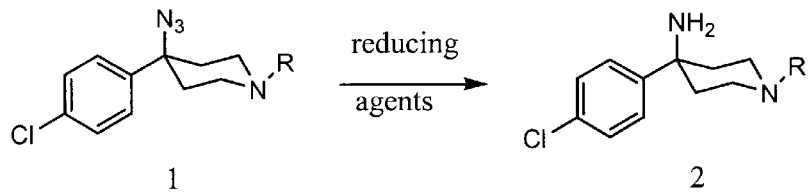
FIG. 9A is a schematic showing the preparation of compounds represented by Structural Formulas (I), (VIII) and (VIII) wherein $R^1$ is an amine.

FIGS. 9A shows the preparation of compounds represent by Structural Formula (I) wherein $R^1$ is an amine. The azido functionality can be reduced with a variety of reducing agents such as triphenylphosphine, lithium aluminum hydride, sodium borohydride, in a solvent such as tetrahydrofuran or diethyl ether in reaction temperature ranges from 0° C. to reflux with a reaction time of between 5 minutes and 72 hours.

Figure 9B:
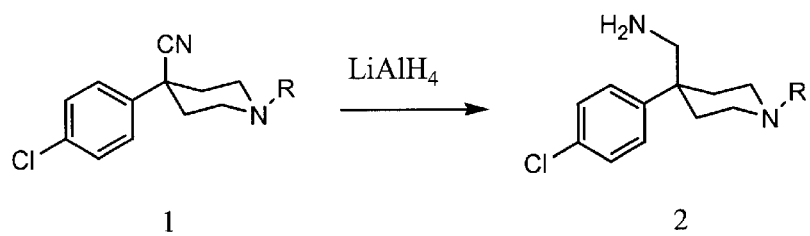
FIG. 9B is a schematic showing the preparation of compounds represented by Structural Formulas (I), (VIII) and (VIII) wherein $R^1$ is an alkylamine.

FIG. 9B shows the preparation of compounds represent by Structural Formula (I) wherein $R^1$ is $-CH2NH_2$. To a cold (0° C.) stirred solution of cyano containing molecule (0,50 g, 0.14 mmol) in a solvent such as diethyl ether or THF (5 mL) can be added a reducing agent such as lithium aluminum hydride (8 mg, 0.21 mmol). The reaction can then be stirred at 0° C. to reflux from 5 minutes to 72 hours. The reaction can then be quenched by the careful addition of $H_2O$ (0.21 mL), 15% aqueous KOH (0.21 mL). The organic payer can then be separated and dried over $Na_2SO_4$. Pure amino compound can be obtained via silica gel flash chromatography.

Figure 9C:
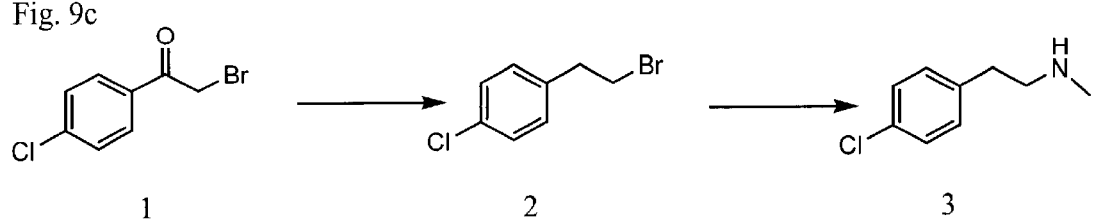
FIG. 9C is a schematic showing the preparation of 2-(4-chlorophenyl)-1-(N-methyl)ethylamine.

FIG. 9C shows the preparation of 2-(4-chlorophenyl)-1-(N-methyl)ethylamine.

Step 1

To a solution of $AlCl_3$ (1.96 g, 14.7 mmol) in anhydrous $CH_2Cl_2$ (50 mL), Borane-tert-butyl amine complex (2.57 g, 29.6 mmol) was added at 0° C. under argon protection, stirred for 10 minutes and clear solution was formed. 4-Chlorophenacyl bromide (1, 1.11 g, 4.91 mmol) in $CH_2Cl_2$ (5 mL) was added to the resulted mixture at 0° C. The reaction was stirred for 1.5 hours and then quenched by the addition of 0.1 N HCl (25 mL). The mixture was extracted with EtOAc (80 mL×3), dried over MgSO4 and concentrated in vacuo. Chromatographic purification on silica gel (Hexane/EtOAc=9:1) provided 0.85 g (84%) of 2-(4-chlorophenyl)-1-bromoethylene (2). MS m/z: (M+ 219).

Step 2

A mixture of 2-(4-chlorophenyl)-1-bromoethylene (2, 1.02 g, 4.62 mmol), EtOH (3 mL) and $H_2NMe$ in $H_2O$ (6 mL, 40% w/w) was heated at 135 0° C. over night. The mixture was cooled down to room temperature. The mixture was extracted with $Et_2O$ (5 mL×2), dried over $MgSO_4$ and concentrated in vacuo. Chromatographic purification on silica gel ($CH_2Cl_2/MeOH/NH_4OH=9/1/0.1$) provided 0.61 g 2-(4-chlorophenyl)-1-(N-methyl)ethylamine (3, 79%). MS m/z: (M+ 170).

Figure 9D:
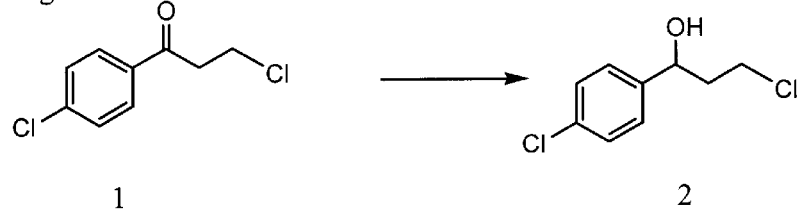
FIG. 9D is a schematic showing the preparation of 3-(4-chlorophenyl)-3-chloro-1-hydroxypropane.

FIG. 9D shows the preparation of 3-(4-chlorophenyl)-3-hydroxyl-3-methyl-1-N-methylaminopropane Step 1

To 3,4'-Dichloropropylphenone (1, 1.10 g, 5.40 mmol) in anhydrous THF at 0° C. under the protection of argon, was added MeMgBr (2.50 mL, 7.35 mmol) dropwise at 0° C. The reaction was stirred at room temperature for an additional hour. The reaction was quenched by adding saturated aqueous $NH_4Cl$. The reaction was then extracted with $Et_2O$ (60 mL×2), dried over $MgSO_4$ and concentrated in vacuo. Chromatographic purification on silica gel (Hexane/EtOAc=10/1) provided 1.0 g (85%) of 3-(4-chlorophenyl)-3-hydroxy-3-methyl-1-bromoropane (2). MS m/z: (M+ 219).

Step 2

A mixture of 3,3,3-(4-Chlorophenyl)-hydroxylmethyl-1-bromoropane (2, 1.04 g, 4.74 mmol), EtOH (5 mL) and $H_2NMe$ in $H_2O$ (10 mL, 40% w/w) was heated at 135 0° C. for 3 hours. The mixture was cooled down to room temperature. The mixture was extracted with $Et_2O$ (5 mL×2), dried over $MgSO_4$ and concentrated in vauco. Chromatographic purification on silica gel ($CH_2Cl_2/MeOH/NH_2OH=9/1/0.1$) provided 1.01 g 3-(4-chlorophenyl)-3-hydroxyl-3-methyl-1-N-methylaminopropane (3, 99%). MS m/z: (M+ 214).

Figure 9E:
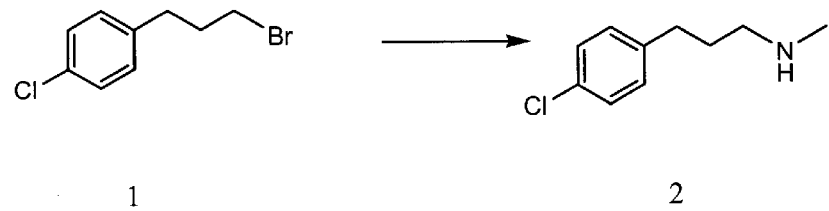
FIG. 9E is a schematic showing the preparation of 3-(4-chlorophenyl)-1-N-methylaminopropane.

FIG. 9E shows the preparation of 3-(4-chlorophenyl)-1-N-methylaminopropane.

A mixture of 3-(4-chlorophenyl)-1-bromoropane (1, 0.70 g, 3.73 mmol), EtOH (3 mL) and $H_2NMe$ in $H_2O$ (6 mL, 40% w/w) was heated at 135 0° C. overnight. The mixture was then cooled down to room temperature. The mixture was extracted with $Et_2O$ (5 mL×2), dried over $MgSO_4$ and concentrated in vacuo. Chromatographic purification on silica gel ($CH_2Cl_2/MeOH/NH_4OH=9/1/0.1$) provided 0.5 g (76%) of 3-(4-chlorophenyl)-1-N-methylaminopropane (2). MS m/z: (M+ 189).

Figure 10A:
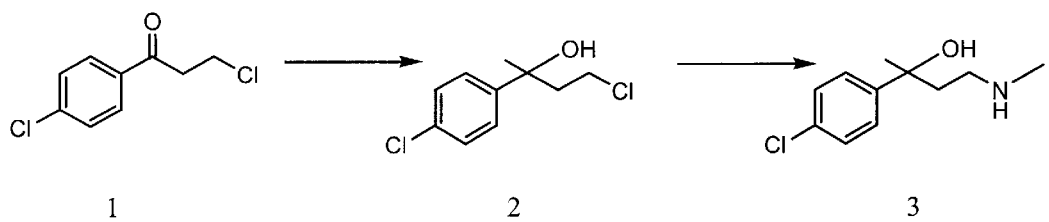
FIG. 10A is a schematic showing the preparation of 3-(4-chlorophenyl)-3-hydroxyl-3-methyl-1-N-methylaminopropane.

FIG. 10A shows the preparation of 3-(4-chlorophenyl)-3-hydroxyl-3-methyl-1-N-methylaminopropane.

Step 1

To 3,4'-Dichloropropylphenone (1, 1.10 g, 5.40 mmol) in anhydrous THF at 0° C. under the protection of argon, was added MeMgBr (2.50 mL, 7.35 mmol) dropwise at 0° C. The reaction was stirred at room temperature for an additional hour. The reaction was quenched by adding saturated aqueous $NH_4Cl$. The reaction was then extracted with $Et_2O$ (60 mL×2), dried over $MgSO_4$ and concentrated in vacuo. Chromatographic purification on silica gel (Hexane/EtOAc= 10/1) provided 1.0 g (85%) of 3-(4-chlorophenyl)-3-hydroxy-3-methyl-1-bromoropane (2). MS m/z: (M+ 219).

Step 2

A mixture of 3,3,3-(4-Chlorophenyl)-hydroxylmethyl-1-bromoropane (2, 1.04 g, 4.74 mmol), EtOH (5 mL) and $H_2NMe$ in $H_2O$ (10 mL, 40% w/w) was heated at 135 0° C. for 3 hours. The mixture was cooled down to room temperature. The mixture was extracted with $Et_2O$ (5 mL×2), dried over $MgSO_4$ and concentrated in vauco. Chromatographic purification on silica gel ($CH_2Cl_2$/MeOH/$NH_2OH$= 9/1/0.1) provided 1.01 g 3-(4-chlorophenyl)-3-hydroxyl-3-methyl-1-N-methylaminopropane (3, 99%). MS m/z; (M+ 214).

Figure 10B:
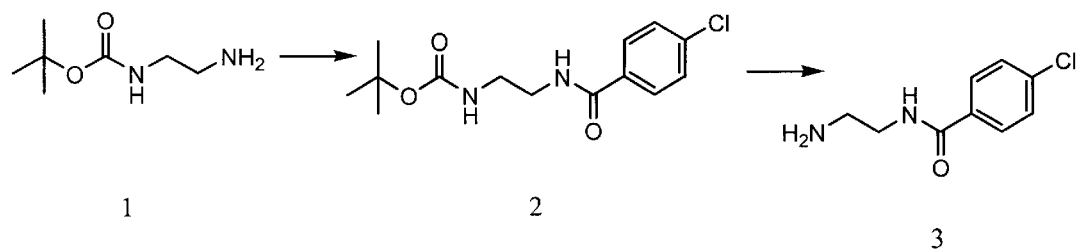
FIG. 10B is a schematic showing the preparation of 1-(4-chlorobenzoyl)-1,3-propylenediamine.

FIG. 10b shows the preparation of 1-(4-chlorobenzoyl)-1,2-ethylenediamine

Step 1 tert-Butyl N-(2-aminoethyl) carbamate (1, 0.50 g g, 3.12 mmol) was added to the mixture of 4-chlorobenzoic acid chloride (0.547 g, 3.12 mmol) and $Et_3N$ (1.74 mL, 12.5 mmol) in $CH_2Cl_2$ (20 mL) under the protection of argon. Stirring at room temperature for 2 hours. The reaction mixture was diluted with $H_2O$ (25 mL), extracted with $CH_2Cl_2$ (50 mL×2), dried over $MgSO_4$ and concentrated in vacuo. Chromatographic purification on silica gel ($CH_2Cl_2$/MeOH=95/5) to provide 0.86 g (2, 93%) of the desired product tert-Butyl 3-(4-chlorobenzoyl)-1-(2-aminoethyl) carbamate. MS m/z: (M+ 299).

Step 2

Trifluoroacetic acid (7.5 mL) was added to the solution of tert-Butyl 3-(4-chlorobenzoyl)-1-(2-aminoethyl)carbamate (2, 0.86 g, 2.89 mmol) in $CH_2Cl_2$ (35 mL) at 0° C. Stirring at room temperature for 30 minutes. Concentration in vacuo provided 0.88 g (95%) of the desired product 1-(4-chlorobenzoyl)-1,2-ethylenediamine (3). MS m/z: (M+ 199).

Compounds prepared according to the schemes presented in FIGS. 9C–9E, 10A and 10B can be used to prepare compounds represented by Structural Formula (VI).

Figure 10C:
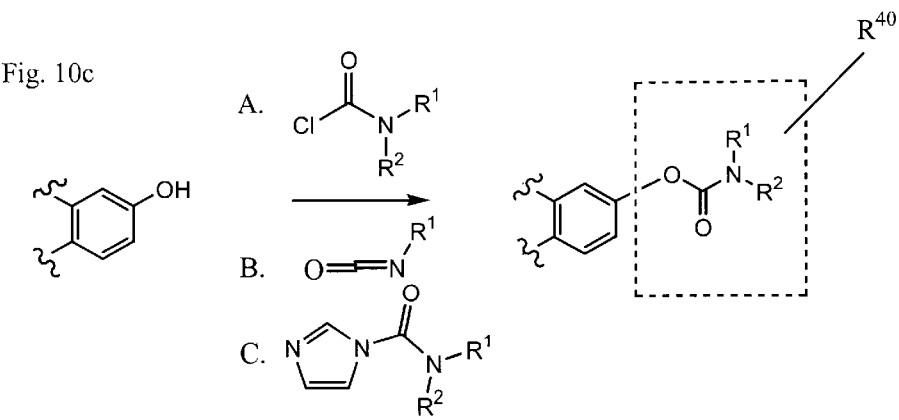
FIG. 10C is a schematic showing three procedures for the preparation of compounds represented by Structural Formulas (I), (VII), (VIII), (IX) and (XI) wherein Z is represented by Structural Formula (III) and wherein Ring A or Ring B in Z is substituted with $R^{40}$.
Figure 10D:
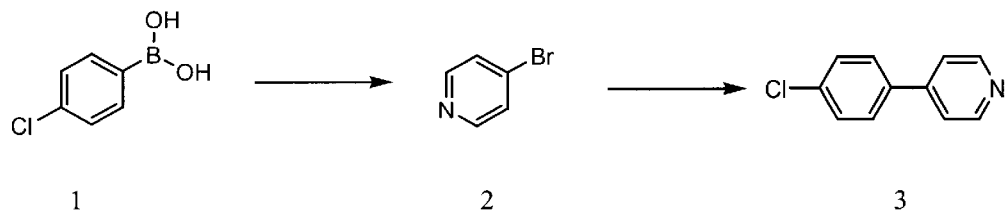
FIG. 10D is a schematic showing the preparation of 4-(4-chlorophenyl)-4-pyridine.
Figure 11A:
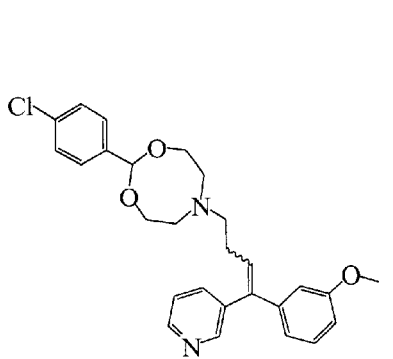
FIGS. 11A–11K show the structures of exemplary compounds of the present invention.
Figure 11A:
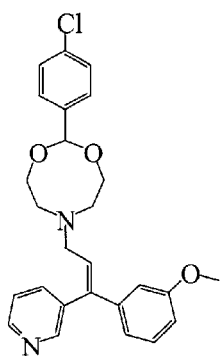
Figure 11A:
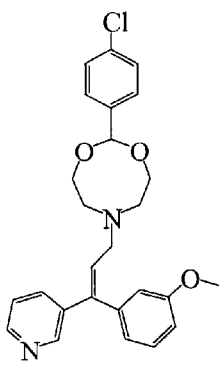
Figure 11A:
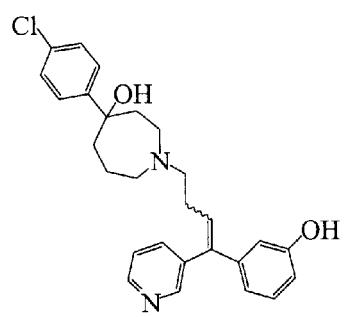
Figure 11A:
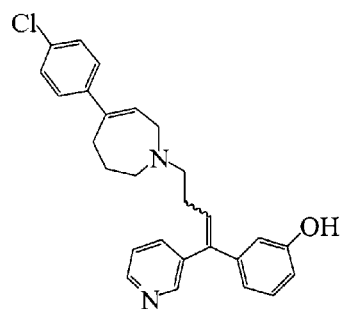
Figure 11A:
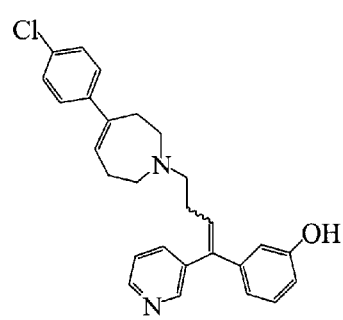
Figure 11A:
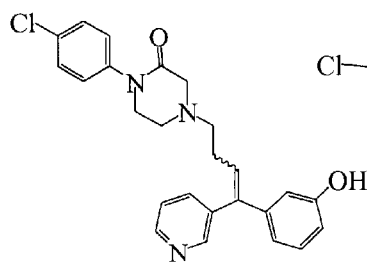
Figure 11A:
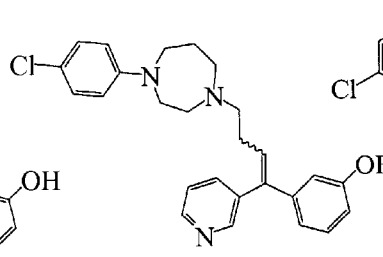
Figure 11A:
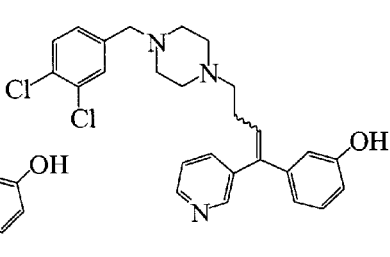
Figure 11A:
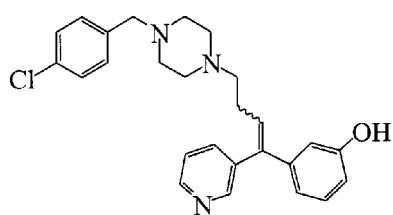
Figure 11A:
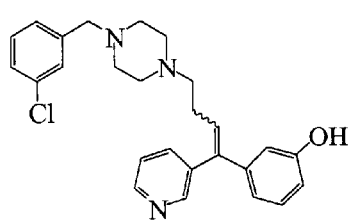
Figure 11B:
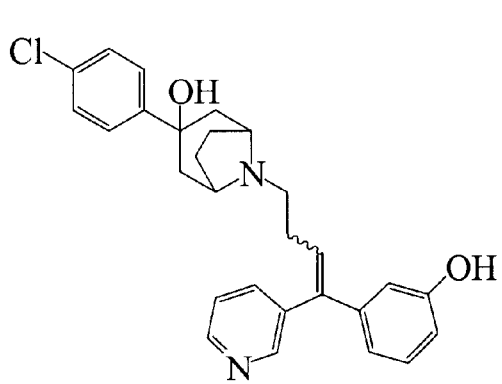
Figure 11B:
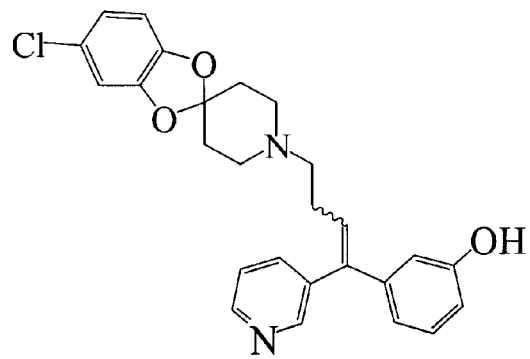
Figure 11B:
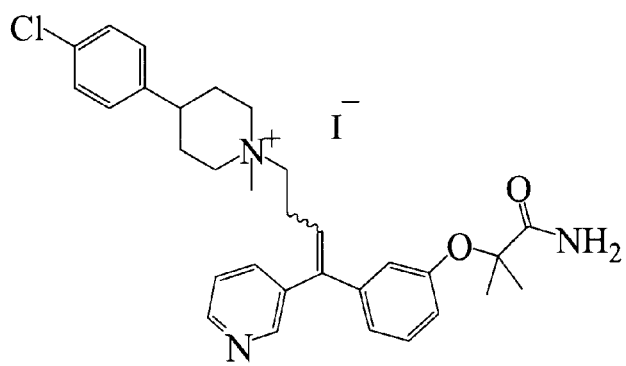
Figure 11C:
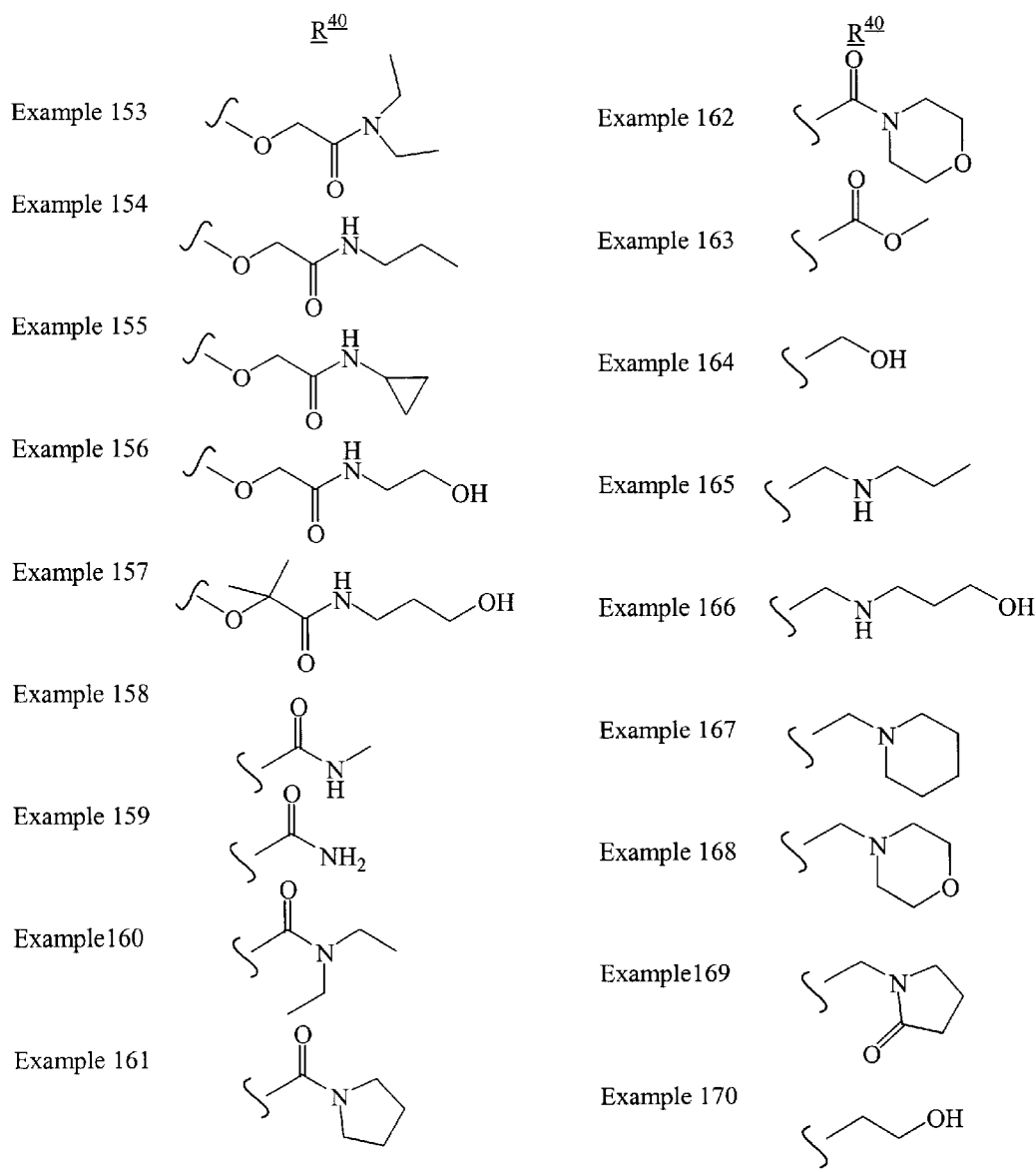
Figure 11D:
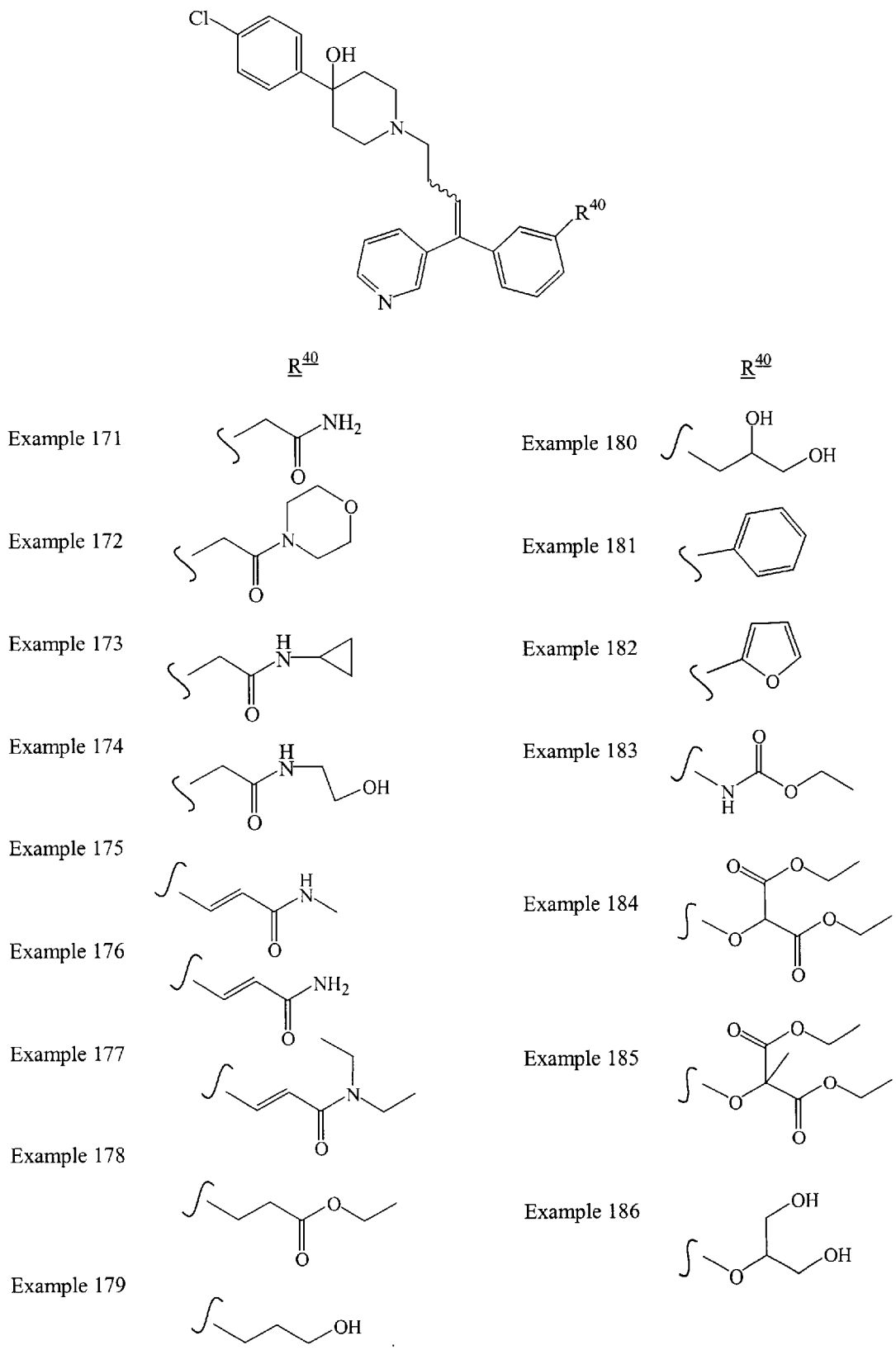
Figure 11E:
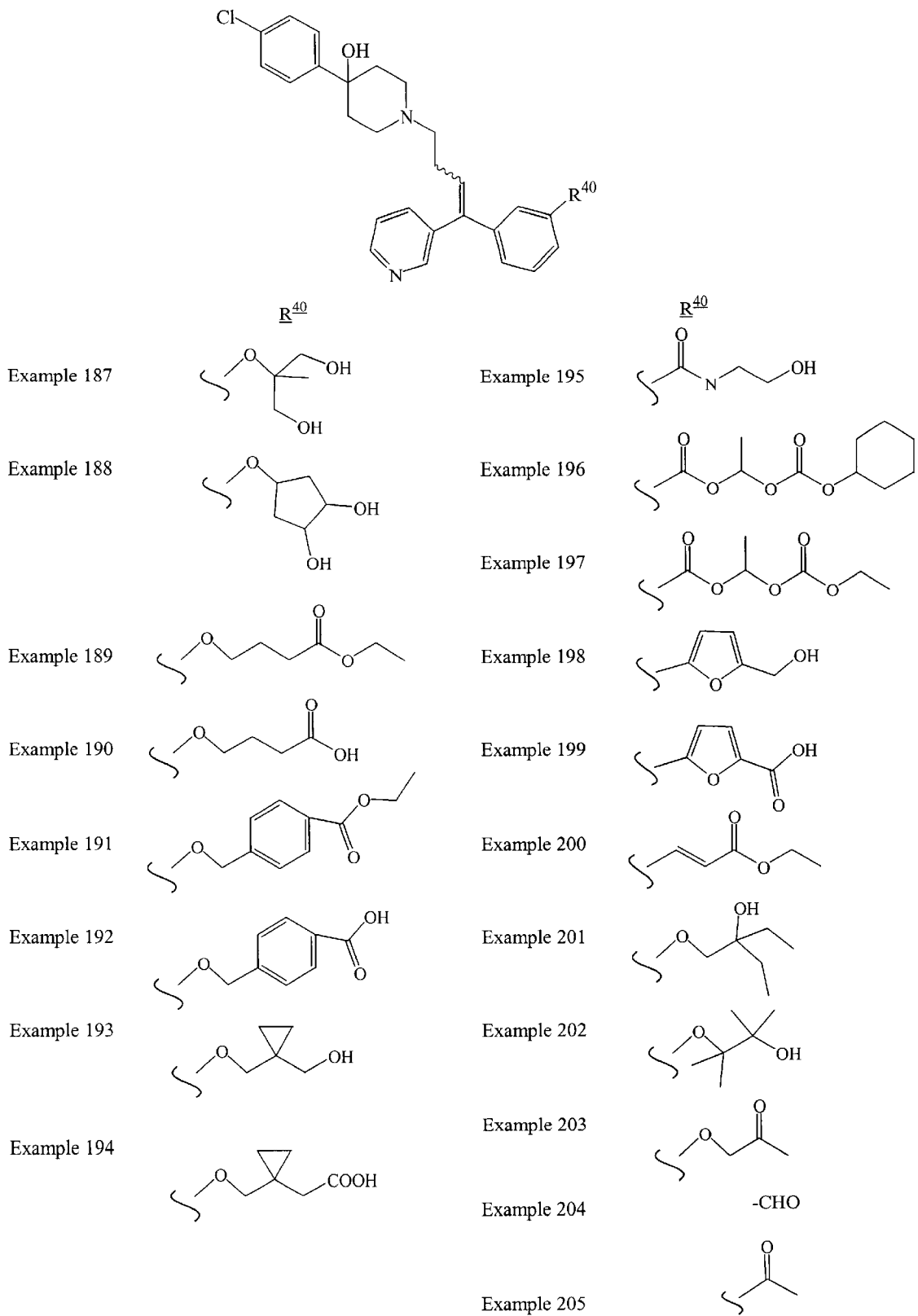
Figure 11F:
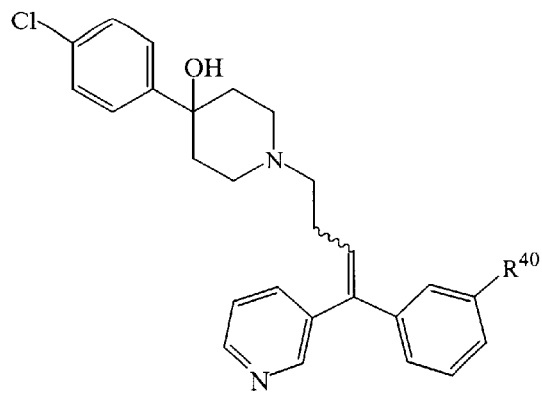
Figure 11F:
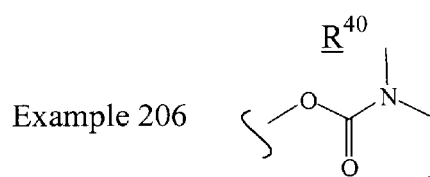
Figure 11F:
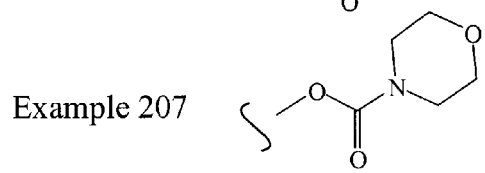
Figure 11F:
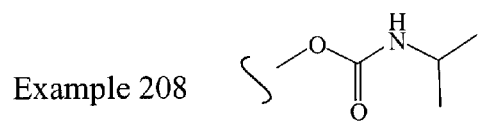
Figure 11F:
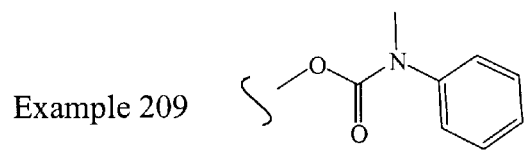
Figure 11F:
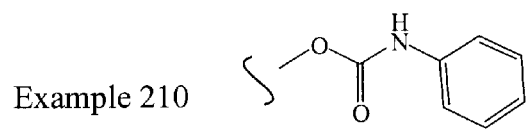
Figure 11F:
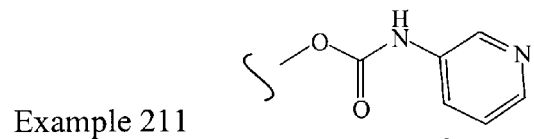
Figure 11F:
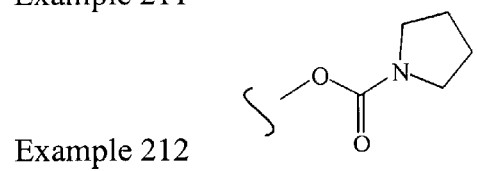
Figure 11G:
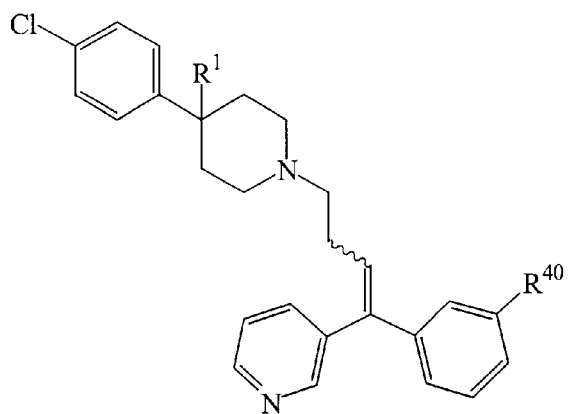
Figure 11G:
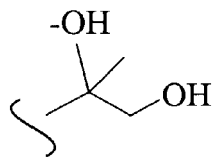
Figure 11H:
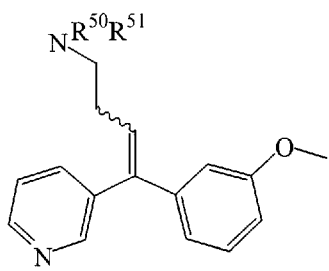
Figure 11H:
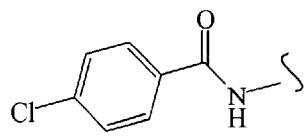
Figure 11H:
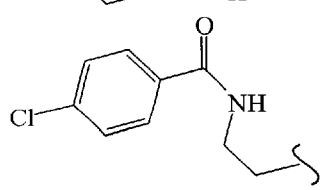
Figure 11H:
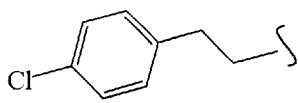
Figure 11H:
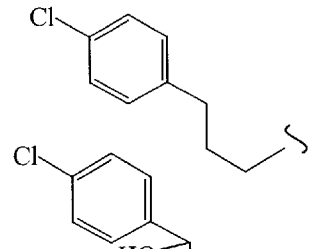
Figure 11H:
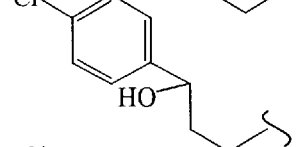
Figure 11H:
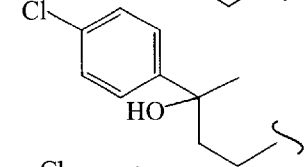
Figure 11H:
Figure 11I:
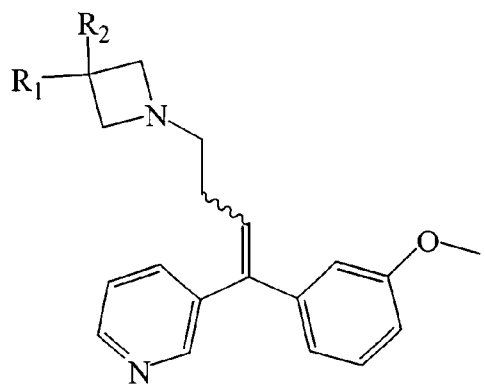
Figure 11I:
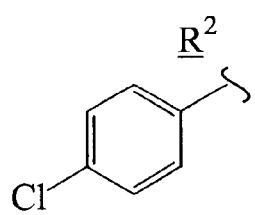
Figure 11I:
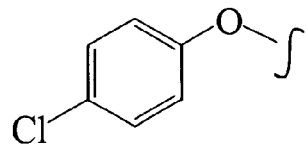
Figure 11I:
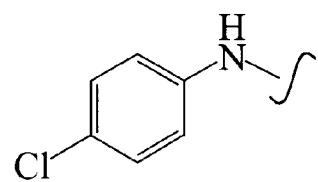
Figure 11I:
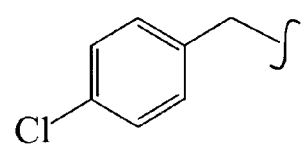
Figure 11I:
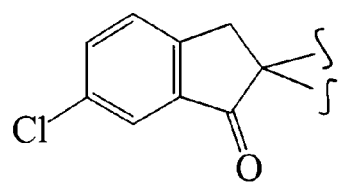
Figure 11J:
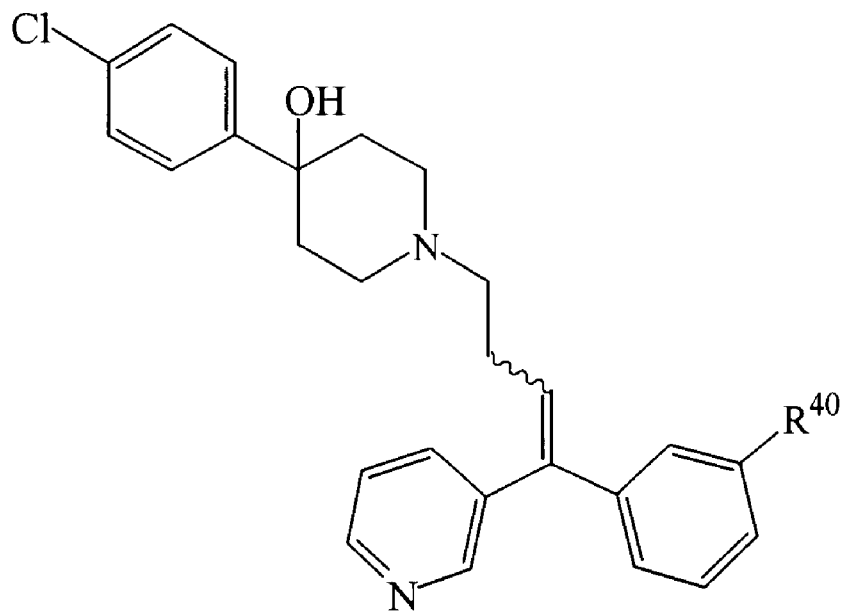
Figure 11J:
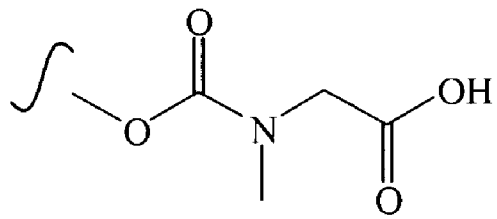
Figure 11J:
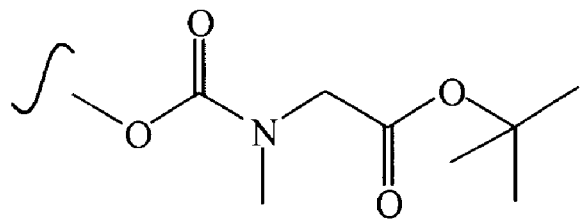
Figure 11K:
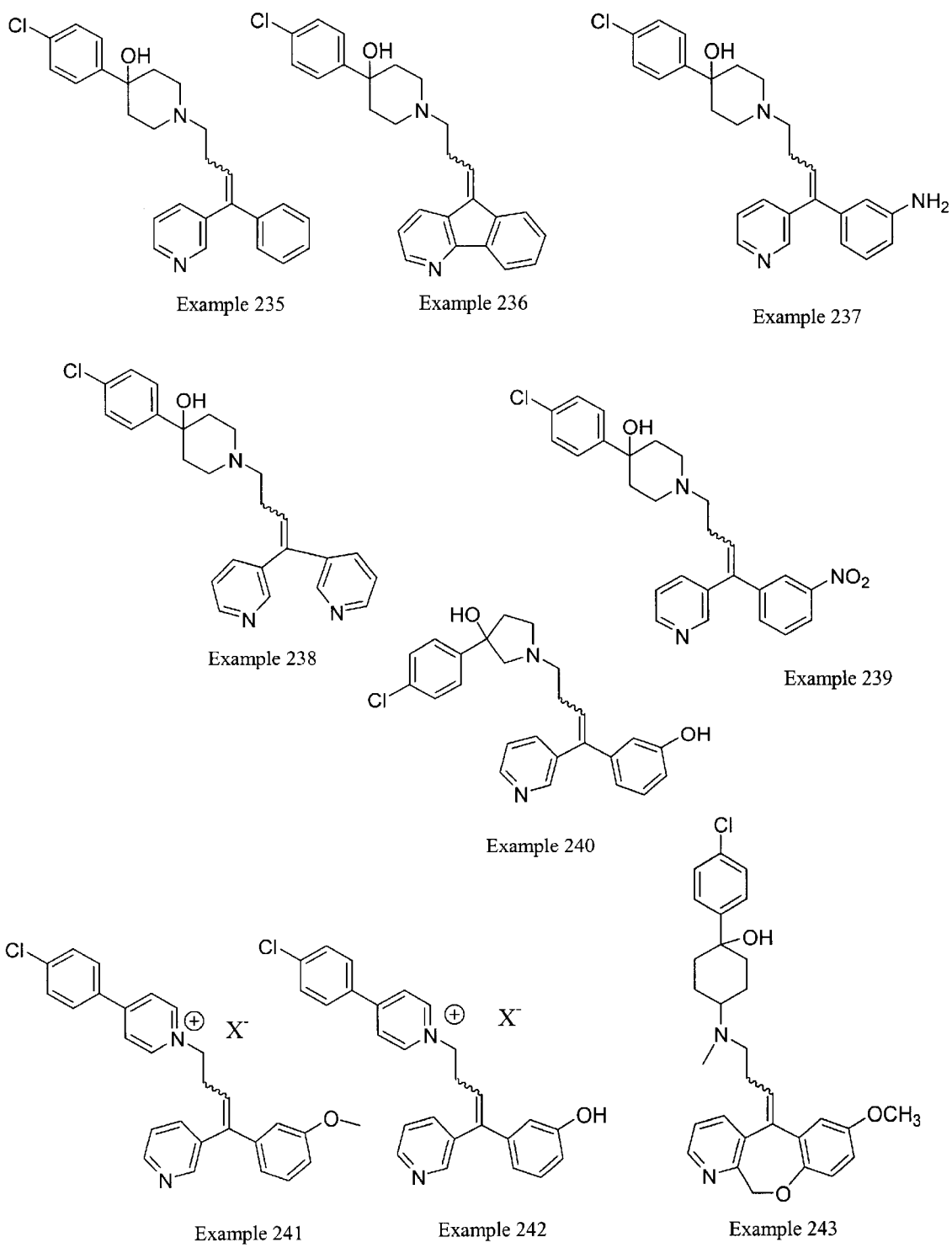

FIG. 10C shows three procedures for the preparation of compounds represented by Structural Formulas (I), (VII), (VIII) and (IX), wherein Z is represented by Structural Formula (III) and wherein Ring A or Ring B in Z is substituted with $R^{40}$. In FIG. 10C, $R^{40}$ is represented by —(O)$_u$—(CH$_2$)$_t$—C(O)—NR$^{21}$R$^{22}$, u is one, t is zero.

In FIG. 10C a compound containing a phenol can be reacted with a carbonate equivalent, such as a carbamoyl chloride (method A), an isocyanate (method B) or an acylimidazole (method C), in the presence of a base such as sodium hydroxide, potassium carbonate or sodium carbonate in a solvent such as dimethylformamide or tetrahydrofuran, at a temperature from 0° C. to reflux temperature for a period of about 5 minutes to about 72 hours.

Although FIGS. 1–5 and 7 show the preparation of compounds in which $Ar^1$ is 3-pyridyl and $Ar^2$ is phenyl, analogous compounds with other heteroaryl groups for $Ar^1$ and/or $Ar^2$ can be prepared by using starting materials with heteroaryl groups in the corresponding positions. These starting materials can be prepared according to methods which are known to those of skill in the art.

The invention is illustrated by the following examples which are not intended to be limiting in any way.

EXEMPLIFICATION

Example 1

4-(4-Chlorophenyl)-1-[4-(3-methoxyphenyl)-4-(3-pyridinyl)-3-butenyl]piperidin-4-ol Step 1

To a solution of (3-methoxyphenyl)-(3-pyridinyl) methanone (500 mg) in THF (10 ml) was added 1.1M cyclopropylmagnesium bromide THF solution (2 ml) at 0° C. The reaction mixture was warmed to room temperature, and stirred for 30 minutes. Aqueous ammonium chloride and ethyl acetate were added to the reaction mixture, the organic layer was separated and washed with saturated aqueous sodium chloride, and dried with magnesium sulfate. The solvent was distilled off under reduced pressure. The residue was filtered and washed with ethyl acetate-hexane (1:2) to give cyclopropyl-(3-methoxyphenyl)-(3-pyridinyl)methanol (470 mg).

$^1$H-NMR (CDCl$_3$) δ: 0.45–0.59 (4H, m), 1.48–1.61 (1H, m), 3.65 (1H, brs), 3.71 (3H, s), 6.78 (1H, dd), 6.92–7.22 (4H, m), 7.69 (1H, dd), 8.27 (1H, dd), 8.55 (1H, d).

Step 2

To a solution of the product of step 1 (470 mg) in acetic acid (5 ml) was added 48% aqueous HBr (3 ml) at 10° C. The reaction mixture was warmed to room temperature, and stirred for 12 hours. Water and ethyl acetate were added to the reaction mixture and neutralized with dilute NaOH solution. The organic layer was separated and washed with saturated aqueous sodium chloride, and dried over magnesium sulfate. The solvent was distilled off under reduced pressure. The residue was purified by silica gel chromatography eluting with ethyl acetate-hexane (1:4) to give 4-bromo-1-(3-methoxyphenyl)-1-(3-pyridinyl)-1-butene (560 mg).

$^1$H-NMR (CDCl$_3$) δ: 2.66–2.74 (2H, m), 3.41–3.46 (2H, m), 3.67 (0.6×3H, s), 3.79 (0.4×3H, s), 6.15–6.18 (1H, m), 6.73–6.80 (3H, m), 7.17–7.47 (3H, m), 8.46–8.64 (2H, m).

Step 3

To a solution the product of step 2 (500 mg) in DMF (20 ml) were added 4-(4-chlorophenyl)-4-hydroxypiperidine (500 mg), potassium carbonate (430 mg), potassium iodide (130 mg) and the mixture was stirred at room temperature for 12 hours. Water and ethyl acetate were added to the reaction mixture, the organic layer wag separated and washed with saturated aqueous sodium chloride, and dried with magnesium sulfate. The solvent was distilled off under reduced pressure. The residue was purified by silica gel chromatography eluting with methylene chloride-methanol (10:1) to give the titled compound as major regioisomer (225 mg) and minor one (140 mg).

Major isomer $^1$H-NMR (CDCl$_3$) δ: 1.65–1.78 (2H, m), 1.98–2.83 (11H, m), 3.79 (3H, s), 6.22 (1H, t), 6.75–6.84 (4H, m), 7.18–7.57 (6H, m), 8.42 (1H, d), 8.50 (1H, dd). MS m/z: 449 (M+1).

Minor isomer $^1$H-NMR (CDCl$_3$) δ: 1.65–1.79 (2H, m), 2.08–2.88 (11H, m), 3.79 (3H, s), 6.12 (1H, t), 6.68–6.94 (4H, m), 7.15–7.53 (6H, m), 8.40 (1H, dd), 8.53 (1H, d). MS m/z: 449 (M+1).

Example 2

4-(4-Chlorophenyl)-1-[4-phenyl-4-(3-pyridinyl)-3-butenyl]piperidin-4-ol

The titled compound was prepared by following the procedure of example 1, but replacing (3-methoxyphenyl)-(3-pyridinyl)methanone with phenyl-(3-pyridinyl) methanone.

Major isomer $^1$H-NMR (CDCl$_3$) δ: 1.67–1.72 (2H, m), 2.07–2.19 (3H, m), 2.31–2.61 (6H, m), 2.75–2.80 (2H, m), 6.18 (1H, t), 7.16–7.48 (11H, m), 8.44 (1H, d), 8.49 (1H, dd). MS m/z: 419 (M+1)

Minor isomer $^1$H-NMR (CDCl$_3$) δ: 1.69–1.74 (2H, m), 2.18–2.23 (3H, m), 2.43–2.66 (6H, m), 2.82–2.86 (2H, m), 6.18 (1H, t), 7.16–7.48 (11H, m), 8.44 (1H, dd), 8.51 (1H, d). MS m/z: 419 (M+1).

Example 3

4-(4-Chlorophenyl)-1-[4-(2,5-dimethoxyphenyl)-4-(3-pyridinyl)-3-butenyl]piperidin-4-ol The titled compound was prepared by following the procedure of example 1, but replacing (3-methoxyphenyl)-(3-pyridnyl)methanone with (2,5-dimethoxyphenyl)-(3-pyridinyl)methanone.

Major isomer $^1$H-NMR (CDCl$_3$) δ: 1.62–1.79 (2H, m), 1.97–2.18 (2H, m), 2.32–2.81 (9H, m), 3.47 (3H, s), 3.79 (3H, s), 5.92 (1H, t), 6.68–6.82 (3H, m), 7.11–7.49 (6H, m), 8.35 (1H, dd), 8.41 (1H, d). MS m/z: 479 (M+1).

Minor isomer $^1$H-NMR (CDCl$_3$) δ: 1.62–1.79 (2H, m), 2.01–2.20 (2H, m), 2.28–2.81 (9H, m), 3.49 (3H, s), 3.80 (3H, s), 5.91 (1H, t), 6.70–6.84 (3H, m), 7.12–7.50 (6H, m), 8.35 (1H, dd), 8.41 (1H, d). MS m/z: 479 (M+1).

Example 4

1-[4-(2-Bromo-4-pyridinyl)-4-(3-pyridinyl)-3-butenyl]-4-(4-chlorophenyl)piperidin-4-ol The titled compound was prepared by following the procedure of example 1, but replacing (3-methoxyphenyl)-(3-pyridinyl)methanone with (2-bromo-4-pyridinyl)-(3-pyridinyl)methanone.

$^1$H-NMR (CDCl$_3$) δ: 1.65–1.70 (2H, m), 1.92–2.18 (5H, m), 2.38–2.54 (4H, m), 2.67–2.72 (2H, m), 6.31 (1H, t), 7.14–7.41 (7H, m), 8.38–8.41 (2H, m), 8.52 (1H, d), 8.75 (1H, s). MS m/z: 500 (M+1).

Examples 5–90 and 91–120 can be prepared by the schemes set forth is FIGS. 1–5 and 7 and the procedures described above.

Example 121

Membrane Preparations for Chemokine Binding and Binding Assays

Membranes were prepared from THP-1 cells (ATCC #TIB202). Cells were harvested by centrifugation, washed twice with PBS (phosphate-buffered saline), and the cell pellets were frozen at −70 to −85° C. The frozen pellet was thawed in ice-cold lysis buffer consisting of 5 mM HEPES (N-2-hydroxyethylpiperazine-N'-2-ethane-sulfonic acid) pH 7.5, 2 mM EDTA (ethylenediaminetetraacetic acid), 5 μg/ml each aprotinin, leupeptin, and chymostatin (protease inhibitors), and 100 μg/ml PMSF (phenyl methane sulfonyl fluoride—also a protease inhibitor), at a concentration of 1 to 5×10$^7$ cells/ml. This procedure results in cell lysis. The suspension was mixed well to resuspend all of the frozen cell pellet. Nuclei and cell debris were removed by centrifugation of 400×g for 10 minutes at 4° C. The supernatant was transferred to a fresh tube and the membrane fragments were collected by centrifugation at 25,000×g for 30 minutes at 4° C. The supernatant was aspirated and the pellet was resuspended in freezing buffer consisting of 10 mM HEPES pH 7.5, 300 mM sucrose, 1 μg/ml each aprotinin, leupeptin, and chymostatin, and 10 μg/ml PMSF (approximately 0.1 ml per each 10$^8$ cells). All clumps were resolved using a minihomogenizer, and the total protein concentration was determined using a protein assay kit (Bio-Rad, Hercules, Calif., cat #500-0002). The membrane solution was then aliquoted and frozen at −70 to −85° C. until needed.

Binding Assays—utilized the membranes described above. Membrane protein (2 to 20 μg total membrane protein) was incubated with 0.1 to 0.2 nM $^{125}$I-labeled RANTES or MIP-1α with or without unlabeled competitor (RANTES or MIP-1α) or various concentrations of compounds. The binding reactions were performed in 60 to 100 μl of a binding buffer consisting of 10 mM HEPES pH 7.2, 1 mM CaCl$_2$, 5 mM MgCl$_2$, and 0.5% BSA (bovine serum albumin), for 60 min at room temperature. The binding reactions were terminated by harvesting the membranes by rapid filtration through glass fiber filters (GF/B or GF/C, Packard) which were presoaked in 0.3% polyethyleneimine. The filters were rinsed with approximately 600 μl of binding buffer containing 0.5 M NaCl, dried, and the amount of bound radioactivity was determined by scintillation counting in a Topcount beta-plate counter.

The activities of test compounds are reported in the Table below as IC$_{50}$ values or the inhibitor concentration required for 50% inhibition of specific binding in receptor binding assays using $^{125}$I-RATES or $^{125}$MIP-1α as ligand and THP-1 cell membranes. Specific binding is defined as the total binding minus the non-specific binding; non-specific binding is the amount of cpm still detected in the presence of excess unlabeled Rantes or $^{125}$MIP-1α.

TABLE

| BIOLOGICAL DATA | |
|---|---|
| Example | IC$_{50}$ (μM) |
| 1 | <1 |
| 2 | <1 |
| 3 | <1 |
| 4 | >1 |

Those skilled in the art will be able to recognize, or be able to ascertain, using no more than routine experimentation, many equivalents to the specific embodiments of the invention described herein. Such equivalents are intended to be encompassed by the following claims.

What is claimed:

1. A method of treating a disease associated with aberrant leukocyte recruitment and/or activation mediated by chemokine receptor function comprising administering to a subject in need thereof an effective amount of a chemokine receptor antagonist represented by the following structural formula:

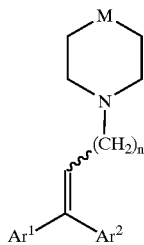

or physiologically acceptable salt thereof, wherein:
Ar$^1$ is a substituted or unsubstituted imidazolyl, thienyl, furanyl, pyridyl, pyrrolyl, pyrimidyl, pyrazinyl, pyridazinyl, pyrazolyl, thiazolyl, tetrazolyl or oxazolyl group;
Ar$^2$ is a substituted or unsubstituted phenyl, naphthyl, anthracyl, imidazolyl, furanyl, pyridyl, pyrrolyl, pyrimidyl, pyrazinyl, pyridazinyl, pyrazolyl, thiazolyl, tetrazolyl or oxazolyl group;
n is an integer from one to four;
M is >CR$^1$R$^2$;
R$^1$ is —H, —OH, —N$_3$, a halogen, an aliphatic group, a substituted aliphatic group, an aminoalkyl group, —O-(aliphatic group), —O-(substituted aliphatic group), —SH, —S-(aliphatic group), —S-(substituted aliphatic group), —OC(O)-(aliphatic group), —O—C(O)-(substituted aliphatic group), —C(O)O-(aliphatic group), —C(O)O-(substituted aliphatic group), —COOH, —CN, —CO—NR$^3$R$^4$, —NR$^3$R$^4$ or R$^1$ is a covalent bond between the ring atom at M and an adjacent carbon atom in the ring which contains M;
R$^2$ is —OH, an acyl group, a substituted acyl group, —NR$^5$R$^6$, a substituted or unsubstituted C$_2$-C$_{20}$ aliphatic group, an aromatic group, a substituted aromatic group, a benzyl group, a substituted benzyl group, a non-aromatic heterocyclic group, a substituted non-aromatic heterocyclic group, —O-(substituted or unsubstituted aromatic group) or —O-(substituted or unsubstituted aliphatic group); wherein
said acyl group is an aliphatic carbonyl, aromatic carbonyl, aliphatic sulphonyl or aromatic sulfonyl;
R$^3$, R$^4$, R$^5$ and R$^6$ are independently —H, an aliphatic group, a substituted aliphatic group, an aromatic group, a substituted aromatic group, a benzyl group, a substituted benzyl group, a non-aromatic heterocyclic group or a substituted non-aromatic heterocyclic group; or
R$^1$ and R$^2$, R$^3$ and R$^4$, or R$^5$ and R$^6$ taken together with the atom to which they are bonded, form a substituted or unsubstituted non-aromatic heterocyclic ring.

2. The method of claim 1 wherein
R$^1$ is —H, —OH, —N$_3$, —CN, a halogen, a substituted aliphatic group, an aminoalkyl group, —O-(aliphatic group), —O-(substituted aliphatic group), —NR$^3$R$^4$ or R$^1$ is a covalent bond between the ring atom at M and an adjacent carbon atom in the ring which contains M;
R$^2$ is —NR$^5$R$^6$, a substituted acyl group, an aromatic group, a substituted aromatic group, a benzyl group, a substituted benzyl group, —O-(substituted or unsubstituted aromatic group); or
R$^1$ and R$^2$ taken together with the atom to which they are bonded, form a substituted or unsubstituted non-aromatic carbocyclic or heterocyclic ring.

3. The method of claim 1 wherein
R$^1$ is a substituted aliphatic group or an aminoalkyl group; and
R$^2$ is —O-(substituted or unsubstituted aromatic group).

4. The method of claim 1 wherein:
Ar$^1$ is a substituted or unsubstituted 3-pyridyl group.

5. The method of claim 4 wherein Ar$^2$ is a substituted or unsubstituted phenyl group.

6. The method of claim 5 wherein said phenyl group bears a meta substituent, R$^{40}$, and the antagonist of chemokine receptor function is represented by the following structural formula:

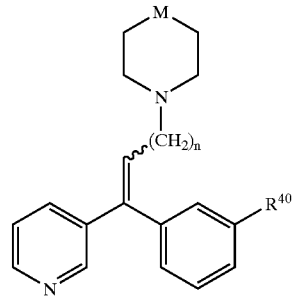

wherein R$^{40}$ is —OH, —COOH, —NO, halogen, aliphatic group, substituted aliphatic group, an aromatic group, a substituted aromatic group, —NR$^{24}$R$^{25}$, —CONR$^{24}$R$^{25}$, Q-(aliphatic group), Q-(substituted aliphatic group), —O-(aliphatic group), —O-(substituted aliphatic group), —O-(aromatic group), —O-(substituted aromatic group), an electron withdrawing group, —(O)$_u$—(CH$_2$)$_t$—C(O)OR$^{20}$, —(O)$_u$—(CH$_2$)$_t$—OC(O)R$^{20}$, —(O)$_u$—(CH$_2$)$_t$—C(O)—NR$^{21}$R$^{22}$ or —(O)$_u$—(CH$_2$)$_t$—NHC(O)O—R$^{20}$; wherein
said electron withdrawing group is alkylimine, alkylsulfonyl, carboxamido, carboxylic alkyl ester, —CH=NH or —NO$_2$;
R$^{20}$, R$^{21}$ or R$^{22}$ are independently —H, an aliphatic group, a substituted aliphatic group, an aromatic group, a substituted aromatic group or a non-aromatic heterocyclic group; or
R$^{21}$ and R$^{22}$, taken together with the nitrogen atom to which they are bonded, form a non-aromatic heterocyclic ring;
Q is —NR$^{24}$C(O)— or —NR$^{24}$S(O)$_2$—;
R$^{24}$ and R$^{25}$ are independently —H, —OH, an aliphatic group or a substituted aliphatic group;
u is zero or one; and
t is an integer from zero to 3.

7. The method of claim 6 wherein R$^{40}$ is —(O)$_u$—(CH$_2$)$_t$—C(O)—NR$^{21}$R$^{22}$.

8. The method of claim 7 wherein u is zero and t is one to three.

9. The method of claim 7 wherein u is one and t is zero.

10. The method of claim 7 wherein u and t are both zero.

11. The method of claim 6 wherein R$^{40}$ is a aliphatic group that is substituted with —NR$^{24}$R$^{25}$ or —CONR$^{24}$R$^{25}$.

12. The method of claim 6 wherein R$^{40}$ is —O-(aliphatic group) or —O-(substituted aliphatic group).

13. The method of claim 6 wherein R$^{40}$ is —COOH.

14. A compound represented by the following structural formula:

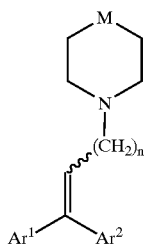

or physiologically acceptable salt thereof, wherein:
  $Ar^1$ is a substituted or unsubstituted imidazolyl, thienyl, furanyl, pyridyl, pyrrolyl, pyrimidyl, pyrazinyl, pyridazinyl, pyrazolyl, thiazolyl, tetrazolyl or oxazolyl group;
  $Ar^2$ is a substituted or unsubstituted phenyl, naphthyl, anthracyl, imidazolyl, furanyl, pyridyl, pyrrolyl, pyrimidyl, pyrazinyl, pyridazinyl, pyrazolyl, thiazolyl, tetrazolyl or oxazolyl group;
  n is an integer from one to four;
  M is $>CR^1R^2$;
  $R^1$ is —H, —OH, —$N_3$, a halogen, an aliphatic group, a substituted aliphatic group, an aminoalkyl group, —O-(aliphatic group), —O-(substituted aliphatic group), —SH, —S-(aliphatic group), —S-(substituted aliphatic group), —OC(O)-(aliphatic group), —O—C(O)-(substituted aliphatic group), —C(O)O-(aliphatic group), —C(O)O-(substituted aliphatic group), —COOH, —CN, —CO—$NR^3R^4$, —$NR^3R^4$ or $R^1$ is a covalent bond between the ring atom at M and an adjacent carbon atom in the ring which contains M;
  $R^2$ is —OH, an acyl group, a substituted acyl group, —$NR^5R^6$, a substituted or unsubstituted $C_2$-$C_{20}$ aliphatic group, an aromatic group, a substituted aromatic group, a benzyl group, a substituted benzyl group, —O-(substituted or unsubstituted aromatic group) or —O-(substituted or unsubstituted aliphatic group); wherein
  said acyl group is an aliphatic carbonyl, aromatic carbonyl, aliphatic sulphonyl or aromatic sulfonyl;
  $R^3$, $R^4$, $R_5$ and $R^6$ are independently —H, an aliphatic group, a substituted aliphatic group, an aromatic group, a substituted aromatic group, a benzyl group, a substituted benzyl group, a non-aromatic heterocyclic group or a substituted non-aromatic heterocyclic group; or
  $R^1$ and $R^2$, $R^3$ and $R^4$, or $R_5$ and $R^6$ taken together with the atom to which they are bonded, form a substituted or unsubstituted non-aromatic heterocyclic ring.

15. The compound of claim 14 wherein:
  $R^1$ is —H, —OH, —$N_3$, —CN, a halogen, a substituted aliphatic group, an aminoalkyl group, —O-(aliphatic group), —O-(substituted aliphatic group), —$NR^3R^4$ or $R^1$ is a covalent bond between the ring atom at M and an adjacent carbon atom in the ring which contains M;
  $R^2$ is —$NR^5R^6$, a substituted acyl group, an aromatic group, a substituted aromatic group, a benzyl group, a substituted benzyl group, —O-(substituted or unsubstituted aromatic group); or
  $R^1$ and $R^2$ taken together with the atom to which they are bonded, form a substituted or unsubstituted non-aromatic carbocyclic or heterocyclic ring.

16. The compound of claim 14 wherein
  $R^1$ is a substituted aliphatic group or an aminoalkyl group; and
  $R^2$ is —O-(substituted or unsubstituted aromatic group).

17. The compound of claim 14 wherein:
  $Ar^1$ is a substituted or unsubstituted 3-pyridyl group.

18. The compound of claim 17 wherein $Ar^2$ is a substituted or unsubstituted phenyl group.

19. The compound of claim 18 wherein said phenyl group bears a meta substituent, $R^{40}$, and said compound is represented by the following structural formula

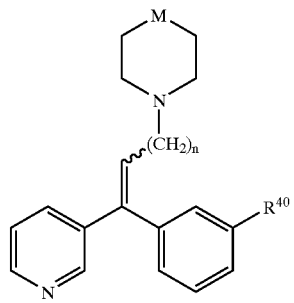

wherein $R^{40}$ is —OH, —COOH, —NO, halogen, aliphatic group, substituted aliphatic group, an aromatic group, a substituted aromatic group, —$NR^{24}R^{25}$, —$CONR^{24}R^{25}$, Q-(aliphatic group),Q-(substituted aliphatic group), —O-(aliphatic group), —O-(substituted aliphatic group), —O-(aromatic group), —O-(substituted aromatic group), an electron withdrawing group, —$(O)_u$—$(CH_2)_t$—$C(O)OR^{20}$, —$(O)_u$—$(CH_2)_t$—$OC(O)R^{20}$, —$(O)_u$—$(CH_2)_t$—$C(O)$—$NR^{21}R^{22}$ or —$(O)_u$—$(CH_2)_t$—$NHC(O)O$—$R^{20}$; wherein
  said electron withdrawing group is alkylimine, alkylsulfonyl, carboxamido, carboxylic alkyl ester, —CH=NH or —$NO_2$;
  $R^{20}$, $R^{21}$ or $R^{22}$ are independently —H, an aliphatic group, a substituted aliphatic group, an aromatic group, a substituted aromatic group or a non-aromatic heterocyclic group; or
  $R^{21}$ and $R^{22}$, taken together with the nitrogen atom to which they are bonded, form a non-aromatic heterocyclic ring;
  Q is —$NR^{24}C(O)$— or —$NR^{24}S(O)_2$—;
  $R^{24}$ and $R^{25}$ are independently —H, —OH, an aliphatic group or a substituted aliphatic group;
  u is zero or one; and
  t is an integer from zero to 3.

20. The compound of claim 19 wherein $R^{40}$ is —$(O)_u$—$(CH_2)_t$—$C(O)$—$NR^{21}R^{22}$.

21. The compound of claim 20 wherein u is zero and t is one to three.

22. The compound of claim 20 wherein u is one and t is zero.

23. The compound of claim 20 wherein u and t are both zero.

24. The compound of claim 19 wherein $R^{40}$ is a aliphatic group that is substituted with —$NR^{24}R^{25}$ or —$CONR^{24}R^{25}$.

25. The compound of claim 19 wherein $R^{40}$ is —O-(aliphatic group) or —O-(substituted aliphatic group).

26. The compound of claim 19 wherein $R^{40}$ is —COOH.

27. The method of claim 1 wherein $R^2$ is a substituted or unsubstituted non-aromatic heterocyclic group, wherein said non-aromatic heterocyclic group is tetrahydrofiuranyl, tetrahyrothiophenyl, morpholino, thiomorpholino, pyrrolidinyl, piperazinyl, piperidinyl, thiazolidinyl, diazolonyl, phthalimidyl, benzoxanyl, benzopyrolidinyl, benzopiperidinyl, benzoxolanyl, benzothiolanyl or benzothianyl.

28. The method of claim 1 wherein $R^2$ is a substituted or unsubstituted $C_2$–$C_{20}$ aliphatic group selected from the group consisting of a substituted or unsubstituted linear $C_2$–$C_{20}$ alkyl, alkenyl or alkynyl group, a substituted or unsubstituted cyclic or branched $C_3$–$C_{20}$ alkyl or alkenyl group, a substituted or unsubstituted branched $C_4$–$C_{20}$ alkynyl group and a substituted or unsubstituted cyclic $C_9$–$C_{20}$ alkynyl group.

29. The method of claim 1 wherein:
$Ar^1$ is 3-pyridyl;
$A^2$ is phenyl;
n is two;
$R^1$ is —H or —OH; and
$R^2$ is 4-chlorophenyl.

30. The method of claim 6 wherein:
n is two;
$R^1$ is —H or —OH; and
$R^2$ is 4-chlorophenyl.

31. The method of claim 7 wherein:
n is two;
$R^1$ is —H or —OH; and
$R^2$ is 4-chlorophenyl.

32. The compound of claim 14 wherein $R^2$ is a substituted or unsubstituted $C_2$–$C_{20}$ aliphatic group selected from the group consisting of a substituted or unsubstituted linear $C_2$–$C_{20}$ alkyl, alkenyl or alkynyl group, a substituted or unsubstituted cyclic or branched $C_3$–$C_{20}$ alkyl or alkenyl group, a substituted or unsubstituted branched $C_4$–$C_{20}$ alkynyl group and a substituted or unsubstituted cyclic $C_9$–$C_{20}$ alkynyl group.

33. The compound of claim 14 wherein:
$Ar^1$ is 3-pyridyl;
$Ar^2$ is phenyl;
n is two;
$R^1$ is —H or —OH; and
$R^2$ is 4-chlorophenyl.

34. The compound of claim 19 wherein:
n is two;
$R^1$ is —H or —OH; and
$R^2$ is 4-chlorophenyl.

35. The compound of claim 20 wherein:
n is two;
$R^1$ is —H or —OH; and
$R^2$ is 4-chlorophenyl.

36. A compound represented by the following structural formula:

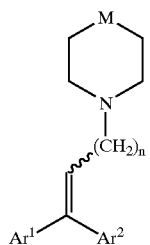

or physiologically acceptable salt thereof, wherein:
$Ar^1$ is a substituted or unsubstituted imidazolyl, thienyl, furanyl, pyridyl, pyrrolyl, pyrimidyl, pyrazinyl, pyridazinyl, pyrazolyl, thiazolyl, tetrazolyl or oxazolyl group;
$Ar^2$ is a substituted or unsubstituted phenyl, naphthyl, anthracyl, imidazolyl, furanyl, pyridyl, pyrrolyl, pyrimidyl, pyrazinyl, pyridazinyl, pyrazolyl, thiazolyl, tetrazolyl or oxazolyl group;
n is an integer from one to four;
M is >$CR^1R^2$;
$R^1$ is —H, —OH, —$N_3$, a halogen, an aliphatic group, a substituted aliphatic group, an aminoalkyl group, —O-(aliphatic group), —O-(substituted aliphatic group), —SH, —S-(aliphatic group), —S-(substituted aliphatic group), —OC(O)-(aliphatic group), —O—C(O)-(substituted aliphatic group), —C(O)-(aliphatic group), —C(O)O-(substituted aliphatic group), —COOH, —CN, —CO—$NR^3R^4$, —$NR^3R^4$ or $R^1$ is a covalent bond between the ring atom at M and an adjacent carbon atom in the ring which contains M;
$R^2$ is a substituted or unsubstituted non-aromatic heterocyclic group, wherein said non-aromatic heterocyclic group is tetrahydrofuranyl, tetrahyrothiophenyl, morpholino, thiomorpholino, pyrrolidinyl, piperazinyl, piperidinyl, thiazolidinyl, diazolonyl, phthalimidyl, benzoxanyl, benzopyrolidinyl, benzopiperidinyl, benzoxolanyl, benzothiolanyl or benzothianyl;
$R^3$ and $R^4$ are independently —H, an aliphatic group, a substituted aliphatic group, an aromatic group, a substituted aromatic group, a benzyl group, a substituted benzyl group, a non-aromatic heterocyclic group or a substituted non-aromatic heterocyclic group; or
$R^1$ and $R^2$, or $R^3$ and $R^4$ taken together with the atom to which they are bonded, form a substituted or unsubstituted non-aromatic heterocyclic ring.

37. The compound of claim 36 wherein:
$Ar^1$ is 3-pyridyl;
$Ar^2$ is phenyl;
n is two; and
$R^1$ is —H or —OH.

* * * * *

UNITED STATES PATENT AND TRADEMARK OFFICE
CERTIFICATE OF CORRECTION

PATENT NO.   : 6,503,926 B2                                          Page 1 of 1
DATED        : January 7, 2003
INVENTOR(S)  : Jay R. Luly et al.

It is certified that error appears in the above-identified patent and that said Letters Patent is hereby corrected as shown below:

Column 29,
Lines 42 and 47, delete "$R_5$" and insert -- $R^5$ --.

Signed and Sealed this

Twenty-fifth Day of March, 2003

JAMES E. ROGAN
*Director of the United States Patent and Trademark Office*